US012623993B2

(12) United States Patent
Smith et al.

(10) Patent No.: US 12,623,993 B2
(45) Date of Patent: May 12, 2026

(54) SYNTHESIS OF VINYL CYCLOBUTYL INTERMEDIATES

(71) Applicant: AMGEN INC., Thousand Oaks, CA (US)

(72) Inventors: Austin G. Smith, Cary, NC (US); Michael T. Corbett, Agoura Hills, CA (US); Neil Fred Langille, Sudbury, MA (US); Kyle D. Baucom, Ventura, CA (US); Peter K. Dornan, Stoneham, MA (US); Gabrielle St- Pierre, Thousand Oaks, CA (US); Philipp C. Roosen, Thousand Oaks, CA (US); Sheng Cui, Lexington, MA (US); Roberto Profeta, Rovigo (IT)

(73) Assignee: AMGEN INC., Thousand Oaks, CA (US)

( * ) Notice: Subject to any disclaimer, the term of this patent is extended or adjusted under 35 U.S.C. 154(b) by 875 days.

(21) Appl. No.: 17/920,084

(22) PCT Filed: May 4, 2021

(86) PCT No.: PCT/US2021/030548
§ 371 (c)(1),
(2) Date: Oct. 20, 2022

(87) PCT Pub. No.: WO2021/226009
PCT Pub. Date: Nov. 11, 2021

(65) Prior Publication Data

US 2023/0183164 A1 Jun. 15, 2023

Related U.S. Application Data

(60) Provisional application No. 63/020,877, filed on May 6, 2020.

(51) Int. Cl.
*C07C 67/62* (2006.01)
*C07D 249/18* (2006.01)
(Continued)

(52) U.S. Cl.
CPC ............ *C07C 67/62* (2013.01); *C07D 249/18* (2013.01); *C07D 513/08* (2013.01); *C07D 519/00* (2013.01); *C07B 2200/13* (2013.01)

(58) Field of Classification Search
CPC ..... C07C 67/62; C07C 2601/04; C07C 67/14; C07C 309/23; C07C 69/76; C07C 303/26;
(Continued)

(56) References Cited

U.S. PATENT DOCUMENTS

| | | | | |
|---|---|---|---|---|
| 9,562,061 | B2 | 2/2017 | Brown et al. | |
| 10,300,075 | B2 | 5/2019 | Brown et al. | |
| 2021/0171543 | A1* | 6/2021 | Chu | C07D 513/22 |

FOREIGN PATENT DOCUMENTS

| | | | |
|---|---|---|---|
| JP | 2023502774 | | 1/2023 |
| WO | 2016/033486 | A1 | 3/2016 |

(Continued)

OTHER PUBLICATIONS

PCT/US2021/030548 International Search Report and Written Opinion (11 pages).

*Primary Examiner* — Laura L Stockton

(57) ABSTRACT

Provided herein are processes for synthesizing intermediates useful in preparing Mcl-1 inhibitors. In particular, provided herein are processes for synthesizing compound F, or a salt thereof, wherein $R^1$ and $OPG^2$ are described herein. Compound F can be useful in synthesizing compound A1, or a salt of solvate thereof, and compound A2, or a salt of solvate thereof.

(F)

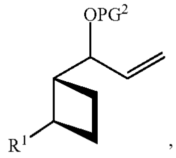

, (A1)

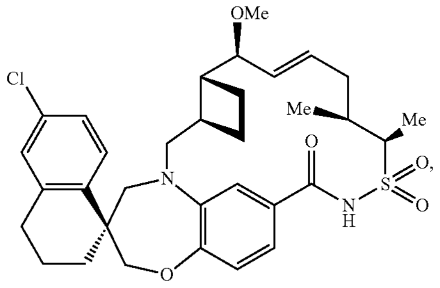

and (A2)

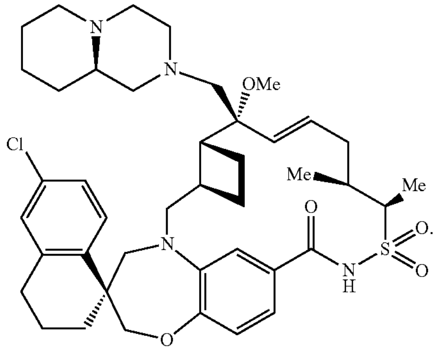

64 Claims, No Drawings

(51) Int. Cl.
*C07D 513/08* (2006.01)
*C07D 519/00* (2006.01)

(58) Field of Classification Search
CPC .. C07C 309/72; C07D 249/18; C07D 513/08; C07D 519/00; C07D 513/10; C07B 2200/13; Y02P 20/55
See application file for complete search history.

(56) References Cited

FOREIGN PATENT DOCUMENTS

| | | | |
|---|---|---|---|
| WO | 2017/147410 | A1 | 8/2017 |
| WO | 2018/183418 | A1 | 10/2018 |
| WO | 2021/096860 | A | 5/2021 |
| WO | 2021108254 | | 6/2021 |

* cited by examiner

SYNTHESIS OF VINYL CYCLOBUTYL INTERMEDIATES

CROSS REFERENCES TO RELATED APPLICATIONS

This application claims the benefit of U.S. Provisional Application No. 63/020,877, filed on May 6, 2020, which is hereby incorporated by reference in its entirety and for all purposes as if fully set forth herein.

BACKGROUND

Technical Field

The present disclosure relates to intermediates and processes for synthesizing intermediates used in synthesizing (1S,3'R,6'R,7'S,8'E,11'S,12'R)-6-chloro-7'-methoxy-11',12'-dimethyl-3,4-dihydro-2H,15'H-spiro[naphthalene-1,22'[20]oxa[13]thia[1,14]diazatetracyclo[14.7.2.$0^{3,6}$.$0^{19,24}$]pentacosa[8,16,18,24]tetraen]-15'-one 13',13'-dioxide (compound A1; AMG 176), a salt, or solvate thereof, and (1S,3'R,6'R,7'R,8'E,11'S,12'R)-6-chloro-7'-methoxy-11',12'-dinethyl-7'-((9aR)-octahydro-2H-pyrido[1,2-a]pyrazin-2-ylmethyl)-3,4-dihydro-2H,15'H-spiro[naphthalene-1,22'-[20]oxa[13]thia[1,14]diazatetracyclo[14.7.2.$0^{3,6}$.$0^{19,24}$]pentacosa[8,16,18,24]tetraen]-15'-one 13',13'-dioxide (compound A2; AMG 397), a salt, or solvate thereof. These compounds are inhibitors of myeloid cell leukemia 1 protein (Mcl-1).

Description of Related Technology

The compound, (1S,3'R,6'R,7'S,8'E,11'S,12'R)-6-chloro-7'-methoxy-11',12'-dimethyl-3,4-dihydro-2H,15'H-spiro[naphthalene-1,22'[20]oxa[13]thia[1,14]diazatetracyclo[14.7.2.$0^{3,6}$.$0^{19,24}$]pentacosa[8,16,18,24]tetraen]-15'-one 13',13'-dioxide (compound A1), is useful as an inhibitor of myeloid cell leukemia 1 (Mcl-1):

(A1)

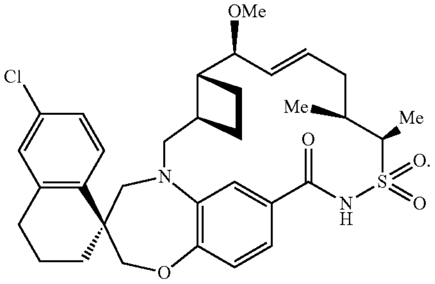

The compound, (1S,3'R,6'R,7'R,8'E,11'S,12'R)-6-chloro-7'-methoxy-11',12'-dinethyl-7'-((9aR)-octahydro-2H-pyrido[1,2-a]pyrazin-2-ylmethyl)-3,4-dihydro-2H,15'H-spiro[naphthalene-1,22'-[20]oxa[13]thia[1,14]diazatetracyclo[14.7.2.$0^{3,6}$.$0^{19,24}$]pentacosa[8,16,18,24]tetraen]-15'-one 13',13'-dioxide (compound A2), is useful as an inhibitor of myeloid cell leukemia 1 (Mcl-1):

(A2)

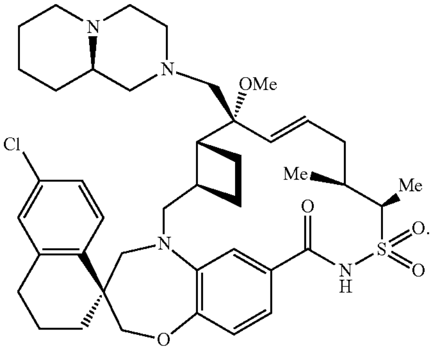

One common characteristic of human cancer is overexpression of Mcl-1. Mcl-1 overexpression prevents cancer cells from undergoing programmed cell death (apoptosis), allowing the cells to survive despite widespread genetic damage.

Mcl-1 is a member of the Bcl-2 family of proteins. The Bcl-2 family includes pro-apoptotic members (such as BAX and BAK) which, upon activation, form a homo-oligomer in the outer mitochondrial membrane that leads to pore formation and the escape of mitochondrial contents, a step in triggering apoptosis. Antiapoptotic members of the Bcl-2 family (such as Bcl-2, Bcl-XL, and Mcl-1) block the activity of BAX and BAK. Other proteins (such as BID, BIM, BIK, and BAD) exhibit additional regulatory functions. Research has shown that Mcl-1 inhibitors can be useful for the treatment of cancers. Mcl-1 is overexpressed in numerous cancers.

U.S. Pat. No. 9,562,061, which is incorporated herein by reference in its entirety, discloses compound A1 as an Mcl-1 inhibitor and provides a method for preparing it. However, improved synthetic methods that result in greater yield and purity of compound A1 are desired, particularly for the commercial production of compound A1.

U.S. Pat. No. 10,300,075, which is incorporated herein by reference in its entirety, discloses compound A2 as an Mcl-1 inhibitor and provides a method for preparing it. However, improved synthetic methods that result in greater yield and purity of compound A2 are desired, particularly for the commercial production of compound A2.

SUMMARY

Provided herein are processes for synthesizing compound F or a salt thereof:

(F)

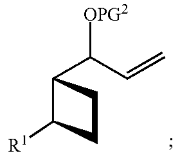

;

wherein $OPG^2$ is a secondary alcohol protecting group and $R^1$ is a protected aldehyde; comprising (a) protecting a secondary alcohol of compound B, or a salt thereof, by reacting compound B, or salt thereof, with an alcohol protecting group reagent to form compound C, or a salt thereof:

(B)

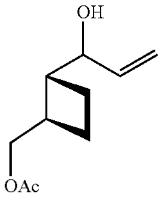

and (C)

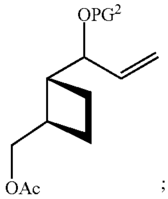

;

(b) removing compound C's acetyl group to form a primary alcohol of compound D, or a salt thereof:

(D)

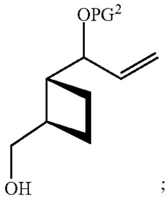

;

(c) oxidizing the primary alcohol of compound D, or salt thereof, to form an aldehyde of compound E, or a salt thereof:

(E)

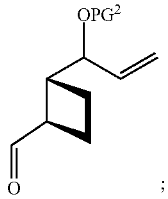

;

and (d) protecting the aldehyde of compound E, or salt thereof, to form a protected aldehyde of compound F, or a salt thereof.

In various embodiments, $OPG^2$ comprises an acyl protecting group, an ether protecting group, acetal or ketal protecting group, a sulfonyl protecting group, and a silyl ether protecting group. In some cases, the acyl protecting group is selected from the group consisting of acetyl, pivaloyl, benzoyl, 4-bromobenzoyl, 4-chlorobenzoyl, 4-iodobenzoyl, 4-fluorobenzoyl, 4-nitrobenzoyl, 4-phenylbenzoyl, 1-naphthoyl, 2-napthoyl, 4-methoxybenzoyl, and isobutyryl. In some cases, the acyl protecting group is 4-bromobenzoyl.

In various embodiments, the alcohol protecting group reagent of step (a) is an acyl chloride or an acyl anhydride.

In various embodiments, compound B and the alcohol protecting group reagent are present in a molar ratio of 1:1 to 1:2. In some cases, the molar ratio of compound B to alcohol protecting group reagent is 1:1.3.

In various embodiments, $OPG^2$ is selected from the group consisting of

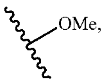

(methoxy)

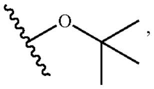

(tert-butyl ether)

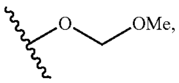

(methoxymethyl acetal, MOM)

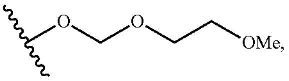

(2-methoxyethoxymethyl ether, MEM)

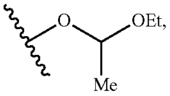

(ethoxyethyl acetal, EE)

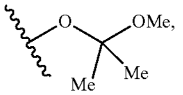

(methoxypropyl acetal, MOP)

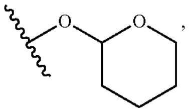

(tetrahydropyranyl acetal, THP)

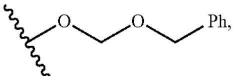

(benzyloxymethyl acetal, BOM)

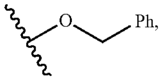

(benzyl ether, Bn)

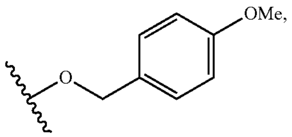

(4-methoxybenzyl ether, PMB)

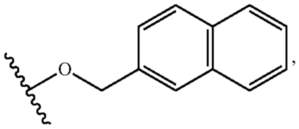

(2-naphthylmethyl ether, Nap)

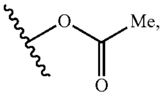

(acetyl, Ac)

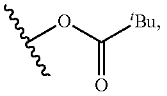

(pivaloyl (Piv)

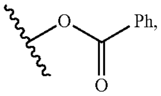

(benzoyl, Bz)

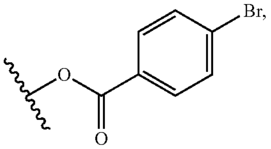

(4-bromobenzoyl, Br-Bz)

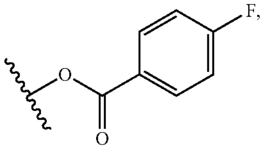

(4-fluorobenzoyl)

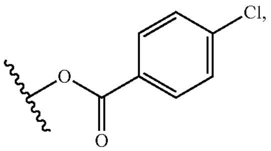

(4-chlorobenzoyl)

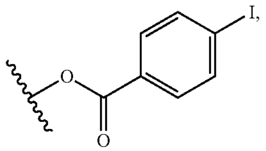

(4-iodobenzoyl)

-continued

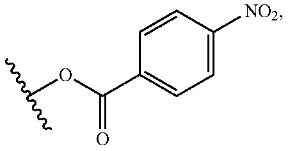

(4-nitrobenzoyl)

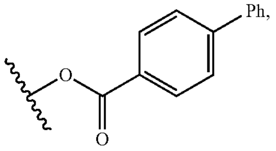

(4-phenylbenzoyl)

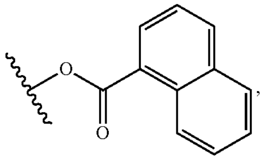, (1-naphthoyl ester)

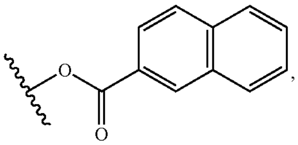, (2-naphthoyl ester)

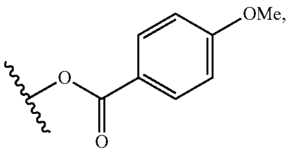

(4-methoxybenzoyl)

,

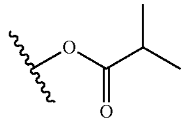

(isobutyryl), $OSO_2Me$ (mesyl)

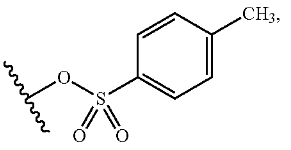

(4-toluenesulfonyl, tosyl)

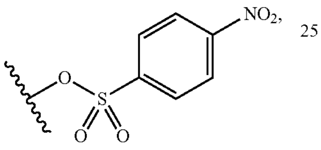

(4-nitrobenzenesulfonyl, nosyl)

and $OSO_2CF_3$ (triflyl). In various embodiments, the silyl ether protecting group is selected from the group consisting of $OSiEt_3$ (triethylsilyl ether, TES), $OSi(^{i}Pr)_3$ (triisopropylsilyl ether, TIPS), $OSiMe_3$ (trimethylsilyl ether, TMS), $OSiMe_2tBu$ (tert-butyldimethylsilyl ether, TBS), and $OSiPh_2{}^{t}Bu$ (tert-butyldiphenylsilyl ether TBDPS).

In various embodiments, step (a) comprises admixing compound B, or salt thereof, the alcohol protecting group reagent, and a nucleophilic catalyst. In various embodiments, the nucleophilic catalyst comprises pyridine, 4-dimethylaminopyridine, or a combination thereof. In various embodiments, compound B and the nucleophilic catalyst are present in a molar ratio of 1:1 to 1:5. In some cases, the molar ratio of compound B to the nucleophilic catalyst is 1:2.

In various embodiments, step (a) occurs in an organic solvent selected from the group consisting of a nonpolar aromatic solvent, an ether solvent, a chlorinated solvent, acetonitrile, dimethylformamide (DMF), methyl isobutyl ketone (MIBK), 2-butanone, acetone, isopropyl acetate (IPAc), ethyl acetate, and a combination thereof. In some cases, the organic solvent is selected from the group consisting of toluene, benzene, xylene, tetrahydrofuran (THF), tetrahydropyran, diethyl ether, dibutyl ether, diisopropyl ether, dimethoxymethane, 1,2-dimethoxyethane, 1,4-dixoane, dichloromethane (DCM), carbon tetrachloride, chloroform, 1,2-dichloroethane, 2-methyltetrahydrofuran (2-MeTHF), methyl tert-butyl ether (MTBE), cyclopentyl methyl ether (CPME), and a combination thereof. In some cases, the organic solvent is toluene, THF, DCM, or a combination thereof.

In various embodiments, step (a) occurs at a temperature of 20° C. to 100° C. In some cases, step (a) occurs at a temperature of 60° C.

In various embodiments, removing the acetyl protecting group in step (b) comprises admixing compound C, or salt thereof, with a deprotecting agent.

In various embodiments, the deprotecting agent comprises acetyl chloride, an enzyme, an acid, a base, a metal hydride, or a combination thereof.

In various embodiments, the deprotecting agent comprises acetyl chloride and an alcohol. In various embodiments, the alcohol is selected from the group consisting of methanol, ethanol, propanol, isopropanol, butanol, and a combination thereof. In some cases, the alcohol is methanol. In various embodiments, the deprotecting agent is magnesium methoxide. In various embodiments, the deprotecting agent is an enzyme selected from the group consisting of an ester hydrolase, a lipase, and a combination thereof. In various embodiments, the deprotecting agent is an acid selected from the group consisting of hydrochloric acid, sulfuric acid, phosphoric acid, and a combination thereof. In various embodiments, the deprotecting agent is zirconium hydride.

In various embodiments, compound C and the deprotecting agent are present in a molar ratio of 1:0.2 to 1:2. In some cases, the molar ratio of compound C to the deprotecting agent is 1:0.5.

In various embodiments, step (b) occurs at a temperature of −15° C. to 25° C. In some cases, step (b) occurs at a temperature of 10° C.

In various embodiments, oxidizing of step (c) comprises admixing compound D, or salt or solvate thereof, and an oxidizing agent, with an organic solvent, and optionally water.

In various embodiments, the oxidizing agent is selected from the group consisting of oxalyl chloride/DMSO, bleach, $SO_3$/pyridine, iodobenzenediacetate, and any combination thereof. In some cases, the oxidizing agent is iodobenzenediacetate.

In various embodiments, compound D and the oxidizing agent are present in a molar ratio of 1:1.1 to 1:2. In some cases, the molar ratio of compound D to the oxidizing agent is 1:1.1.

In various embodiments, the oxidizing further comprises admixing compound D and the oxidizing reagent with an oxidation catalyst. In various embodiments, the oxidation catalyst is selected from the group consisting of 2,2,6,6-tetramethylpiperidin-1-yl)oxidanyl (TEMPO), tetrapropylammonium perruthenate (TPAP)/N-methylmorpholine-N-oxide (NMO), Cu/9-azabicyclo[3.3.1]nonane N-oxyl (ABNO), Fe/ABNO, and a combination thereof. In some cases, the oxidation catalyst is TEMPO.

In various embodiments, compound D and the oxidation catalyst are present in a molar ratio of 1:0.01 to 1:1. In some cases, the molar ratio of compound D to the oxidation catalyst is 1:0.04.

In various embodiments, wherein the organic solvent (of step (c)) is selected from the group consisting of a nonpolar aromatic solvent, an ether solvent, a chlorinated solvent, methyl isobutyl ketone (MIBK), 2-butanone, acetone, isopropyl acetate, ethyl acetate, and a combination thereof. In some cases, the organic solvent is selected from the group consisting of toluene, benzene, xylene, tetrahydrofuran (THF), tetrahydropyran, diethyl ether, dibutyl ether, diisopropyl ether, dimethoxymethane, 1,2-dimethoxyethane, 1,4-dixoane, dichloromethane (DCM), carbon tetrachloride, chloroform, 1,2-dichloroethane, 2-methyltetrahydrofuran (2-MeTHF), methyl tert-butyl ether (MTBE), cyclopentyl methyl ether (CPME), and a combination thereof. In some cases, the organic solvent is toluene.

In various embodiments, step (c) occurs in the presence of water. In various embodiments, compound D and water are present in a molar ratio of 1:1 to 1:2. In some cases, the molar ratio of compound D to water is 1:1.1.

In various embodiments, step (c) occurs at a temperature of 5° C. to 45° C. In some cases, step (c) occurs at a temperature of 20° C.

In various embodiments, protecting the aldehyde of compound E, or salt thereof, in step (d) comprises admixing compound E, or salt thereof, and an aldehyde protecting group reagent with a solvent.

In various embodiments, the aldehyde protecting group reagent is selected from the group consisting of benzotriazole, a bisulfite salt, a cyanide salt, hydrogen cyanide, a thiol or dithiol, an alcohol or diol, hydrazine, ammonia, and a combination thereof. In various embodiments, $R^1$ is selected from the group consisting of

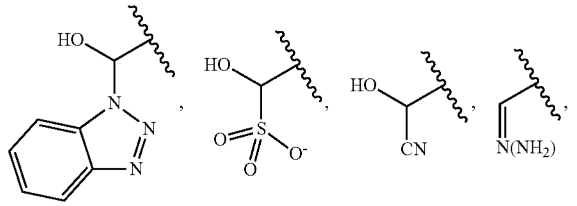

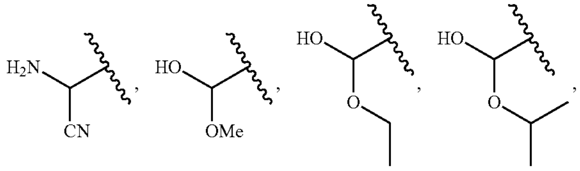

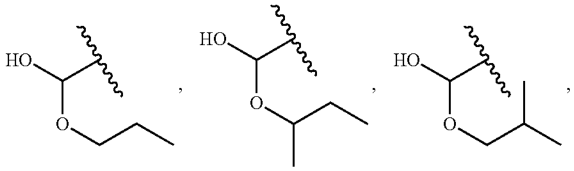

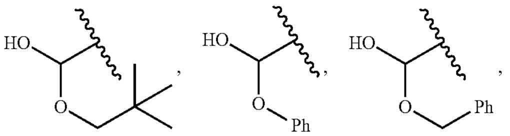

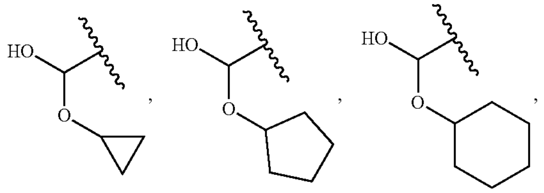

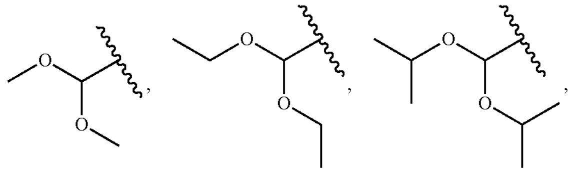

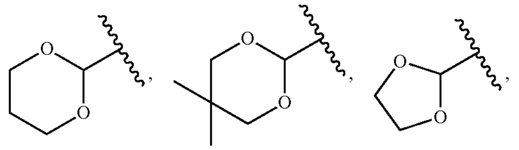

-continued

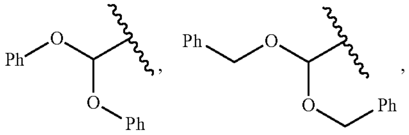

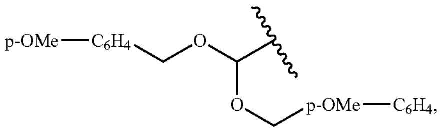

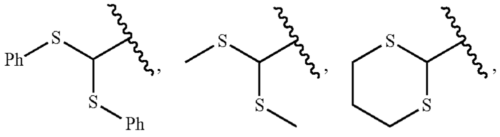

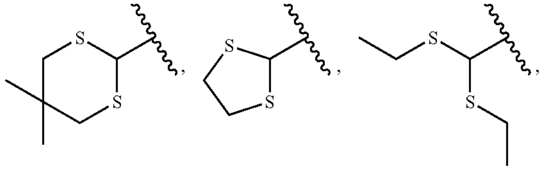

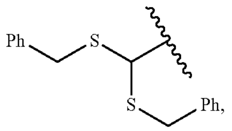

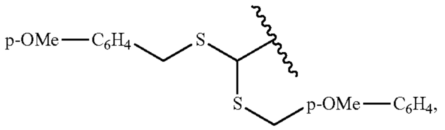

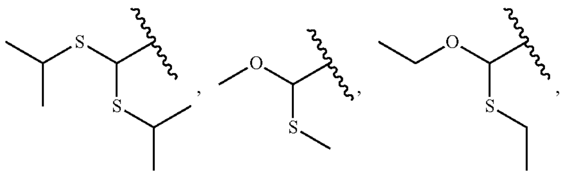

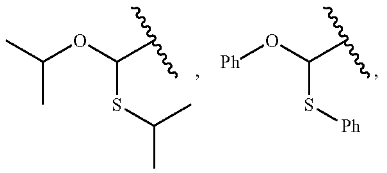

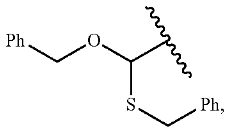

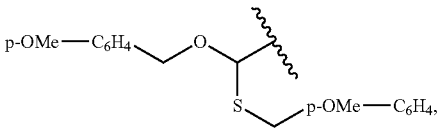

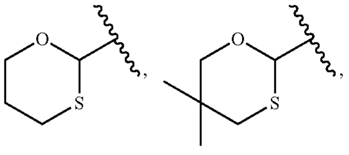 and

-continued

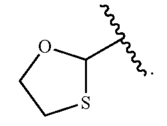

In some cases, $R^1$ is

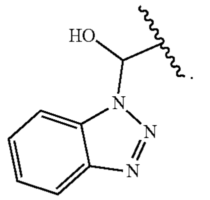 [SMILES: *C(O)n1nnc2ccccc21]

In some cases, $R^1$ is

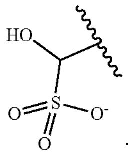 [SMILES: *C(O)S(=O)(=O)[O-]]

In various embodiments, compound E and the aldehyde protecting group reagent are present in a molar ratio of 1:1 to 1:1.5. In some cases, the molar ratio of compound E to the aldehyde protecting group reagent is 1:1.

In various embodiments, the solvent is selected from the group consisting of toluene, heptane, acetonitrile, water, methyl tert-butyl ether (MTBE), and a combination thereof. In various embodiments, the solvent of step (d) is selected from the group consisting of toluene/heptane, acetonitrile/water, and methyl tert-butyl ether (MTBE). In some cases, the solvent is toluene/heptane. In some cases, toluene and heptane are present in the solvent as a volume ratio of 4:7.

In various embodiments, step (d) occurs at a temperature of 20° C. to 50° C.

In various embodiments, the processes further comprise (e) crystallizing compound F.

In various embodiments, crystallizing comprises admixing compound F with a crystallizing solvent to form crystalline compound F. In various embodiments, the crystallizing solvent comprises heptane, toluene, methyl tert-butyl ether (MTBE), cyclopentyl methyl ether (CPME), methyl isobutyl ketone (MIBK), acetonitrile, isopropyl alcohol, isopropyl acetate, water, or a combination thereof.

In various embodiments, the processes further comprise synthesizing compound A1, or a salt or solvate thereof, using compound F:

(A1)

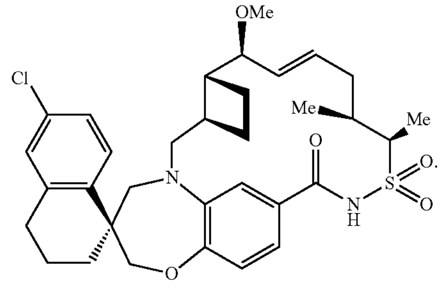

In various embodiments, the processes further comprise synthesizing compound A2, or a salt of solvate thereof, using compound F:

(A2)

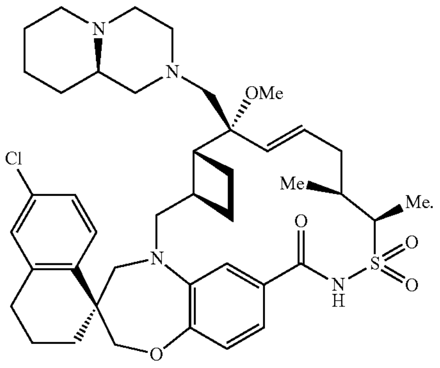

Further provided herein are compounds having the structure of Formula (I):

(I)

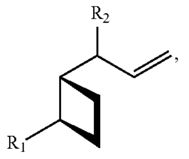

wherein $R^1$ is

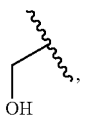

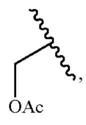

or a protected aldehyde; $R^2$ is OH or $OPG^2$; and $OPG^2$ is a secondary alcohol protecting group, with the proviso that if $R^2$ is OH, then $R^1$ is

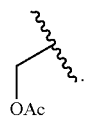

In various embodiments, $R^1$ is
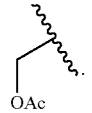.
In various embodiments, $R^1$ is
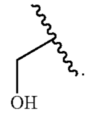.
In various embodiments, $R^1$ is a protected aldehyde. In some cases, $R^1$ is selected from the group consisting of
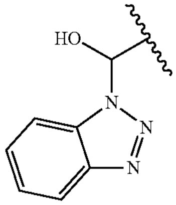, 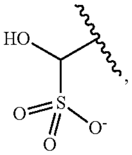, 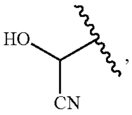, 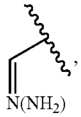,
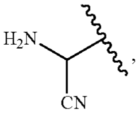, 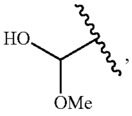, 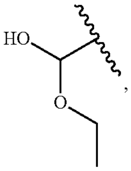, 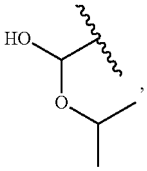,
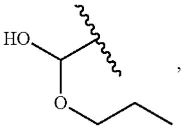, 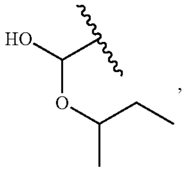, 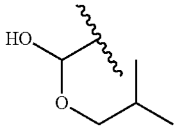,
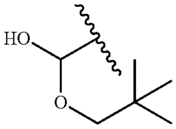, 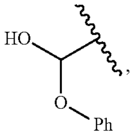, 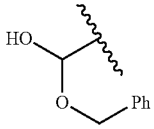,
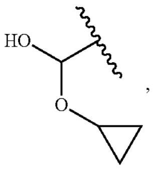, 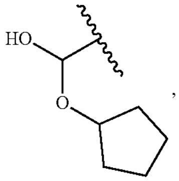, 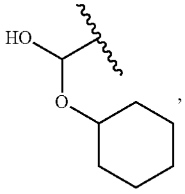,
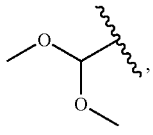, 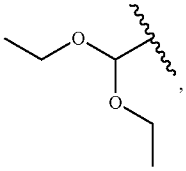, 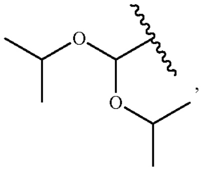,
-continued
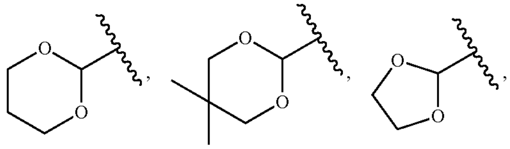,
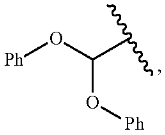, 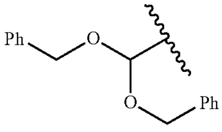,
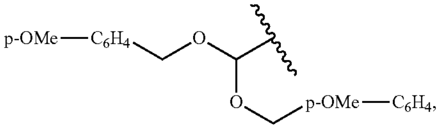,
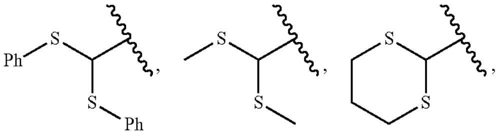,
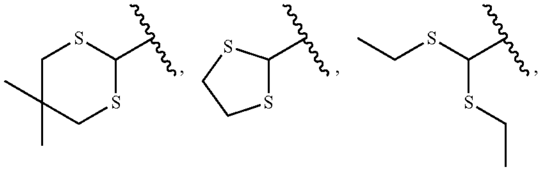,
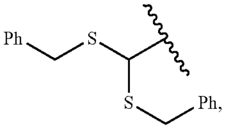,
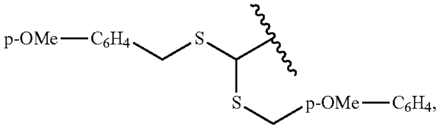,
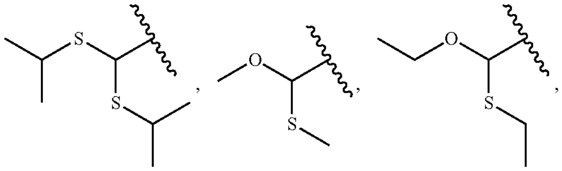,
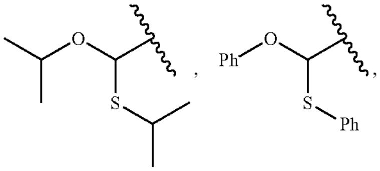,
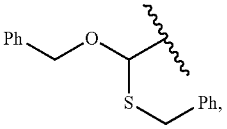,
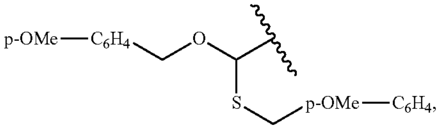, -continued

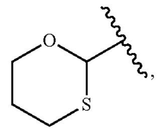
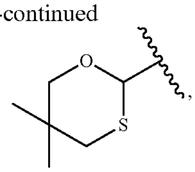
and
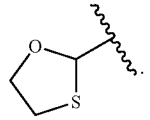

In some cases, $R^1$ is

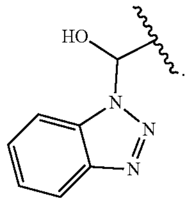 [SMILES: *C(O)n1nnc2ccccc21]

In some cases, $R^1$ is

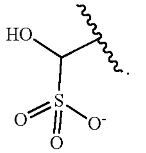

In various embodiments, $R^2$ is OH. In various embodiments, $R^2$ is $OPG^2$. In various embodiments, $OPG^2$ selected from the group consisting of an ether, an acetal or ketal, an acyl, a sulfonyl, and a silyl ether. In some cases, $OPG^2$ is selected from the group consisting of

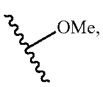
(methoxy)

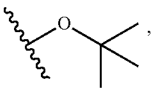
(tert-butyl ether)

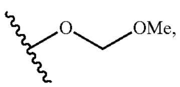
(methoxymethyl acetal, MOM)

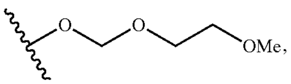
(2-methoxyethoxymethyl ether, MEM)

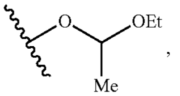
(ethoxyethyl acetal, EE)

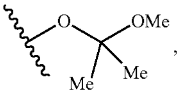
(methoxypropyl acetal, MOP)

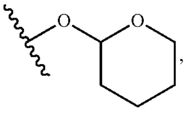
(tetrahydropyranyl acetal, THP)

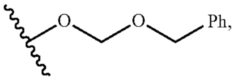
(benzyloxymethyl acetal, BOM)

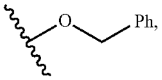
(benzyl ether, Bn)

-continued

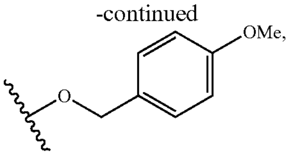
(4-methoxybenzyl ether PMB)

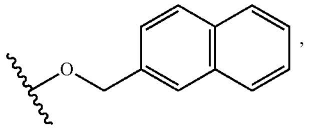
(2-naphthylmethyl ether, Nap)

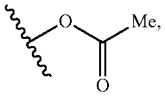
(acetyl, Ac)

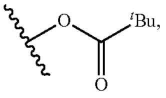
pivaloyl (Piv)

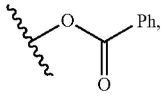
(benzoyl, Bz)

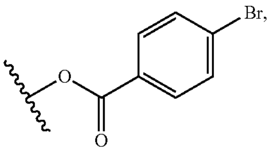
(4-bromobenzoyl, Br-Bz)

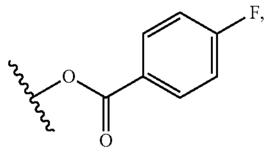
(4-fluorobenzoyl)

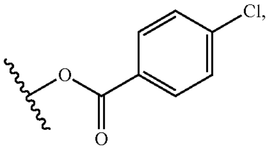
(4-chlorobenzoyl)

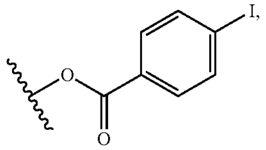
(4-iodobenzoyl)

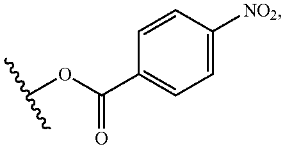
(4-nitrobenzoyl)

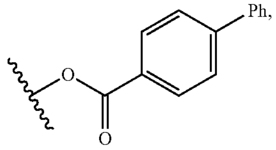
(4-phenylbenzoyl)

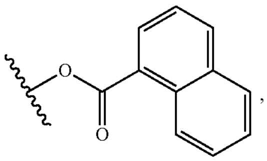
(1-naphthoyl ester)

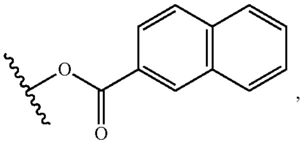
(2-naphthoyl ester)

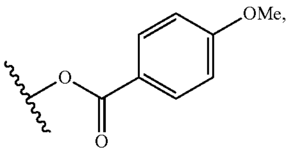
(4-methoxybenzoyl)

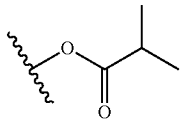
(isobutyryl)

$OSiEt_3$ (triethylsilyl ether, TES), $OSi(^iPr)_3$ (triisopropylsilyl ether, TIPS), $OSiMe_3$ (trimethylsilyl ether, TMS), $OSiMe_2tBu$ (tert-butyldimethylsilyl ether, TBS), $OSiPh_2{}^tBu$ (tert-butyldiphenylsilyl ether TBDPS), $OSO_2Me$ (mesyl),

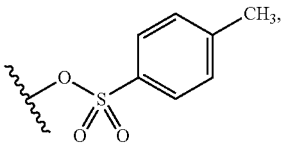

(4-toluenesulfonyl, tosyl)

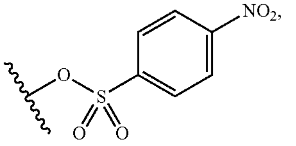

(4-nitrobenzenesulfonyl, nosyl)

and $OSO_2CF_3$ (triflyl). In some cases, $OPG^2$ is 4-bromobenzoyl.

In various embodiments, the compound is selected from the group consisting of:

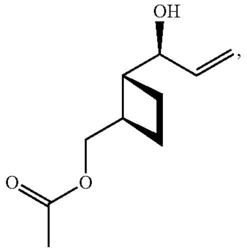

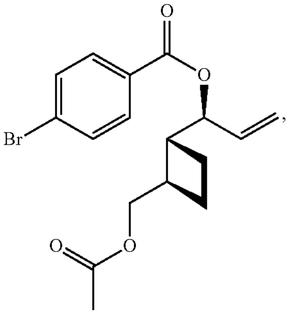

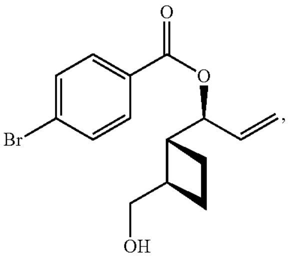

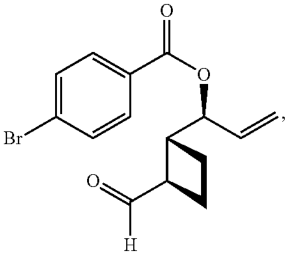

-continued

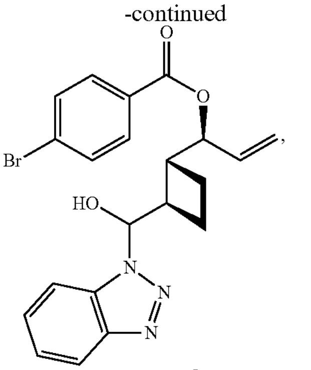

and

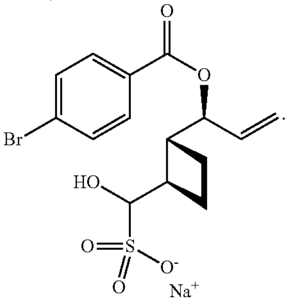

Further aspects and advantages will be apparent to those of ordinary skill in the art from a review of the following detailed description. The description hereafter includes specific embodiments with the understanding that the disclosure is illustrative, and is not intended to limit the invention to the specific embodiments described herein.

DETAILED DESCRIPTION

Provided herein are processes for synthesizing Mcl-1 inhibitors and corresponding vinyl cyclobutyl intermediates. In particular, processes for synthesizing (1S,3'R,6'R,7'S,8'E,11'S,12'R)-6-chloro-7'-methoxy-11',12'-dimethyl-3,4-dihydro-2H,15'H-spiro[naphthalene-1,22'[20]oxa[13]thia[1,14]diazatetracyclo[14.7.2.$0^{3,6}$.$0^{19,24}$]pentacosa[8,16,18,24]tetraen]-15'-one 13',13'-dioxide (compound A1), or a salt or solvate thereof, and for synthesizing (1S,3'R,6'R,7'R,8'E,11'S,12'R)-6-chloro-7'-methoxy-11',12'-dinethyl-7'-((9aR)-octahydro-2H-pyrido[1,2-a]pyrazin-2-ylmethyl)-3,4-dihydro-2H,15'H-spiro[naphthalene-1,22'-[20]oxa[13]thia[1,14]diazatetracyclo[14.7.2.$0^{3,6}$.$0^{19,24}$]pentacosa[8,16,18,24]tetraen]-15'-one 13',13'-dioxide (compound A2), or a salt of solvate thereof are provided:

(A1)

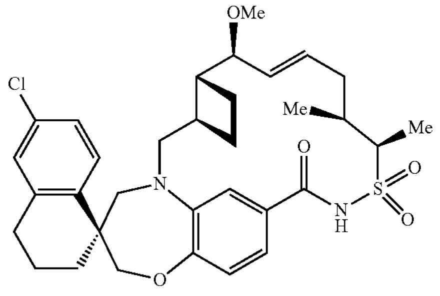

and

-continued (A2)

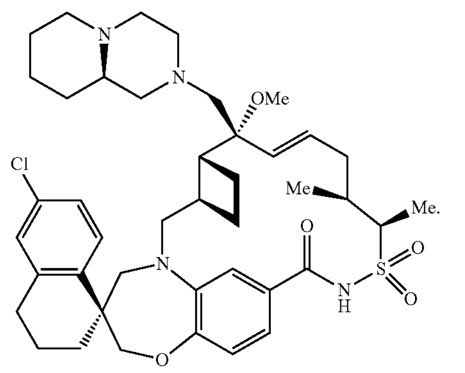

U.S. Pat. No. 9,562,061, which is incorporated herein by reference in its entirety, discloses compound A1, or a salt or solvate thereof, as an Mcl-1 inhibitor and provides a process for preparing it. The disclosure of compound A1 salts and solvates from U.S. Pat. No. 9,562,061 is incorporated by reference in its entirety. This patent also discloses a process of synthesizing a vinylic alcohol intermediate compound shown below used in the synthesis of compound A1.

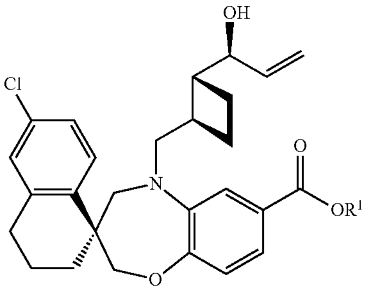

vinylic alcohol intermediate of '061 patent

U.S. Pat. No. 10,300,075, which is incorporated herein by reference in its entirety, discloses compound A2, or a salt or solvate thereof, as an Mcl-1 inhibitor and provides a process for preparing it. The disclosure of compound A2 salts and solvates from U.S. Pat. No. 10,300,075 is incorporated by reference in its entirety.

The ’061 patent generally describes a procedure for making a vinylic alcohol intermediate as shown in Scheme 1, below, which is adapted from the disclosure at col. 49 of the ’061 patent. The ’061 patent describes that the cyclobutane carbaldehyde (intermediate II) is combined with the oxazepine (intermediate I) in a solvent at a temperature below room temperature preferably 0° C. Sodium cyanoborohydride is added, and the mixture is added to a sodium hydroxide solution, thereby providing intermediate Ill. Advantageously, the processes described herein provide an improved synthetic route as compared to General Procedure 1 of the ’061 patent. The processes described herein can be performed at ambient conditions (e.g., room temperature) and with milder reagents. Moreover, the processes can provide a crystalline vinyl cyclobutyl intermediate which allows for improved isolation, storage, and purity compared to the vinyl cyclobutyl intermediate of the ’061 patent.

Scheme 1-General Procedure 1 of the '061 Patent

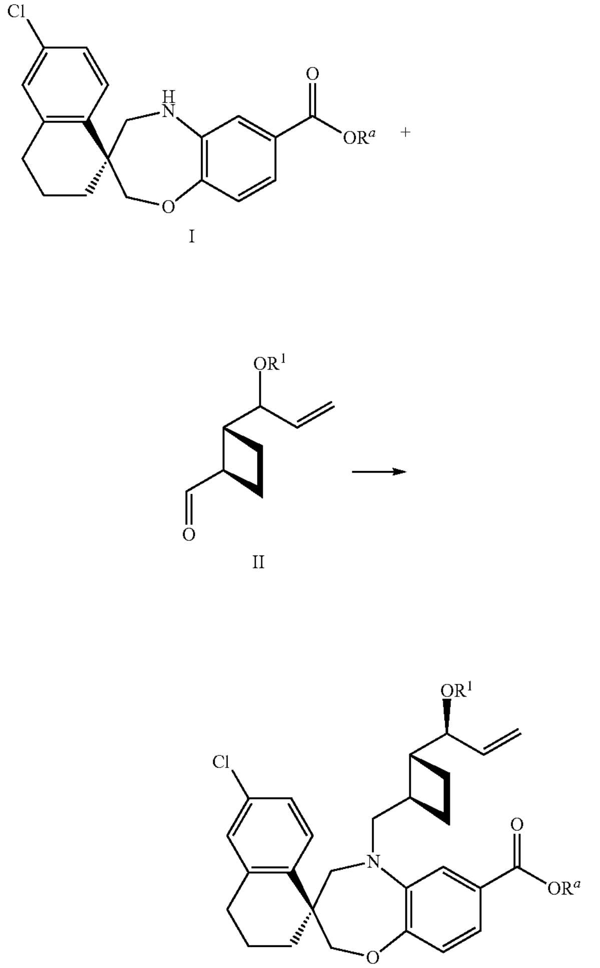

I

II

III $R_1$ = H, $C_{1-6}$alkyl, and $(CH_2CH_2)_nCH_3$

The ’061 patent further describes a process for synthesizing a vinylic alcohol intermediate compound using a cyclobutyl intermediate in which the vinyl group is added to the compound after the fragment including the cyclobutyl intermediate is already joined with the benzoxazepine moiety. For example, Scheme 2, as shown below and adapted from the disclosure at cols. 66-71 of the ’061 patent, represents the general process of synthesizing the vinylic alcohol as described in the ’061 patent, using a cyclobutyl intermediate that does not include a vinylic group. The ’061 patent describes the isolation of each of the intermediate compounds prior to use in the next step of the synthesis. Advantageously, use of the vinyl cyclobutyl intermediates and processes of making the same described herein leads to fewer steps when preparing the vinylic alcohol intermediate, and does not require isolation of any intermediates. Moreover, the vinyl cyclobutyl intermediates and processes of making the same described herein allow for a convergent fragment assembly of compounds A1 and A2, provide a superior purity profile, provide for highly crystalline intermediates, thereby improving stability, and have an overall higher yield, as compared to the ’061 patent.

Scheme 2-Synthesis of Vinylic Alcohol Intermediate of the '061 Patent

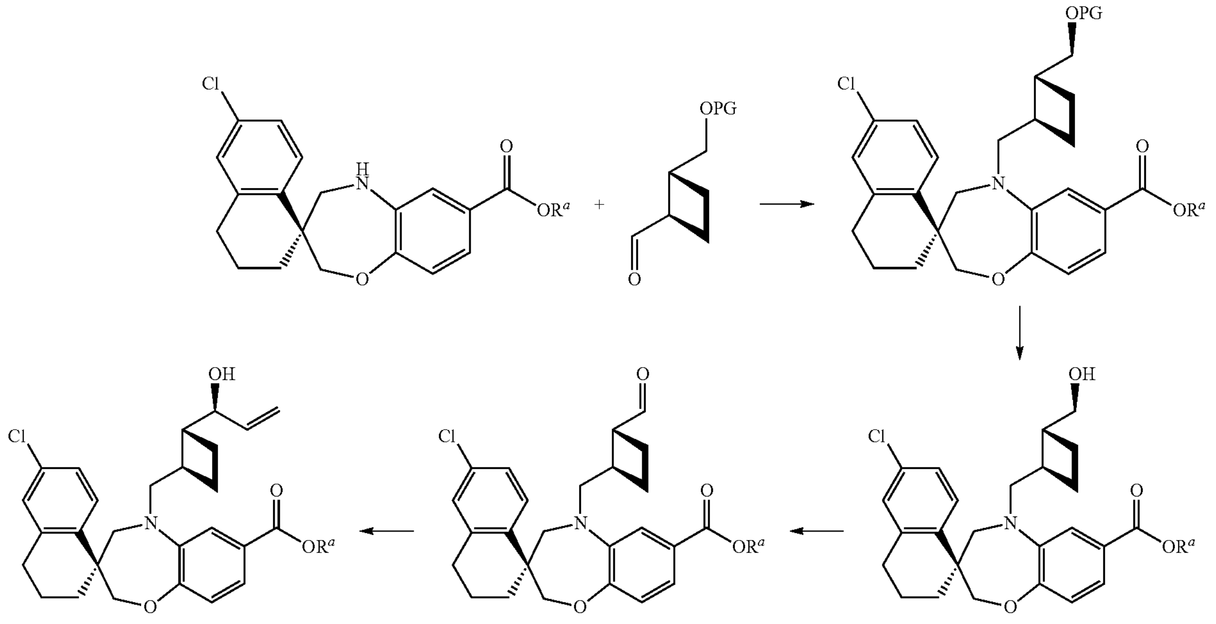

Processes for Synthesizing Vinyl Cyclobutyl Intermediates

The disclosure provides processes for synthesizing compound F or a salt thereof:

(F)

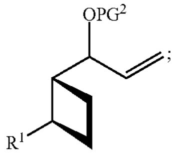

wherein $OPG^2$ is a secondary alcohol protecting group and $R^1$ is a protected aldehyde, the method including: (a) protecting a secondary alcohol of compound B, or a salt thereof, by reacting compound B, or salt thereof, with an alcohol protecting group reagent to form compound C, or a salt thereof:

(B)

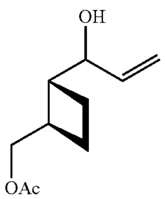

and (C)

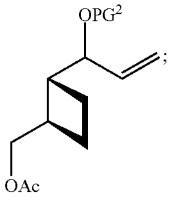

(b) removing compound C's acetyl group to form a primary alcohol of compound D, or a salt thereof:

(D)

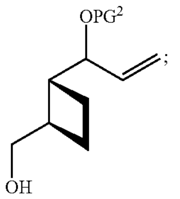

(c) oxidizing the primary alcohol of compound D, or salt thereof, to form an aldehyde of compound E, or a salt thereof:

(E)

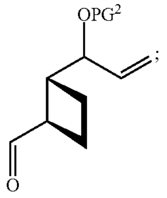

and (d) protecting the aldehyde of compound E, or salt thereof, to form a protected aldehyde of compound F, or a salt thereof.

A general reaction scheme for the processes described herein is provided in Scheme 3, below:

Scheme 3-General Process for Synthesis of Cyclobutyl Intermediates

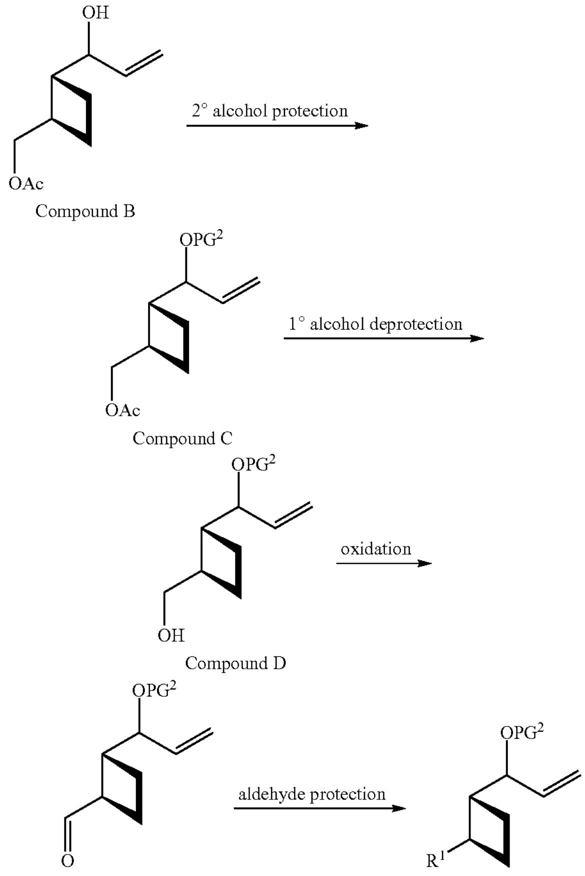

Compound B

Compound C

Compound D

Compound E

Compound F

Protection of Secondary Alcohol

The processes of the disclosure include protecting a secondary alcohol of compound B, or a salt thereof. In particular, compound B, or salt thereof, is reacted with an alcohol protecting group reagent to form compound C, or a salt thereof.

As provided herein, compound B has a structure of

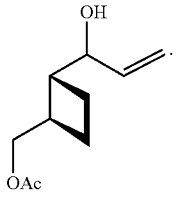

(B)

In some embodiments, compound B is a salt. A salt of compound B, or any other compound described herein, can be prepared, for example, by reacting the compound in its free base form with a suitable organic or inorganic acid, and optionally isolating the salt thus formed. Nonlimiting examples of suitable salts for any one or more of the compounds described herein include hydrobromide, hydrochloride, sulfate, bisulfate, sulfonate, camphorsulfonate, phosphate, nitrate, acetate, valerate, oleate, palmitate, stearate, laurate, benzoate, lactate, phosphate, tosylate, citrate, maleate, fumarate, succinate, tartrate, naphthylate, mesylate, glucoheptonate, lactobionate, laurylsulphonate salts, and amino acid salts, and the like.

Compound B is reacted with an alcohol protecting group reagent, which thereby protects the secondary alcohol of compound B. Alcohol protecting groups are groups that mask a hydroxyl functional group, and are well known in the art. Preparation of compounds can involve the protection and deprotection of various hydroxyl groups. The need for protection and deprotection, and the selection of appropriate protecting groups, and protecting group reagents, can be readily determined by one skilled in the art. The chemistry of protecting groups can be found, for example, in Greene, et al., Protective Groups in Organic Synthesis, 4d. Ed., Wiley & Sons, 2007, which is incorporated herein by reference in its entirety. Adjustments to the alcohol protecting groups and formation and cleavage methods described herein may be adjusted as necessary in light of the various substituents. Nonlimiting examples of suitable alcohol protecting group reagents include acyl halides (e.g., acetyl chloride, pivaloyl chloride, 4-bromobenzoyl chloride, etc.), acyl anhydrides (e.g., acetic anhydride, maleic anhydride, etc.), silyl halides (e.g., trimethylsilyl chloride, chlorotriethylsilane, triisopropylsilyl chloride, etc.), and sulfonyl halides (e.g., methanesulfonyl chloride, etc.). Other alcohol protecting group reagents that can be used to provide the alcohol protecting group, $OPG^2$, as described herein, are also contemplated.

In some embodiments, the alcohol protecting group reagent is an acyl chloride or an acyl anhydride. For example, in some cases, the alcohol protecting group reagent is an acyl chloride, such as 4-bromobenzoyl chloride. In some cases, the alcohol protecting group reagent is an acyl anhydride, such as acetic anhydride.

Compound B and the alcohol protecting group reagent can be present in a molar ratio of 1:1 to 1:2, for example, at least 1:1, 1:1.1, 1:1.2, 1:1.3, 1:1.4, 1:1.5, or 1:1.6, and/or up to 1:2, 1:1.9, 1:1.8, 1:1.7, 1:1.6, 1:1.5, or 1:1.4, such as 1:1 to 1:1.8, 1:1 to 1:1.5, 1:1 to 1:1.4, or 1:1.2 to 1:1.4. In some embodiments, the molar ratio of compound B to the alcohol protecting group reagent is 1:1.3.

In some embodiments, step (a) can include admixing compound B, or salt thereof, the alcohol protecting group reagent, and a nucleophilic catalyst. Nonlimiting examples of nucleophilic catalysts include pyridine, dimethylaminopyridine (DMAP), and N-methylimidazole. In some embodiments, the nucleophilic catalyst includes pyridine, 4-dimethylaminopyridine, or a combination thereof. In some embodiments, the nucleophilic catalyst is pyridine. In some embodiments, the nucleophilic catalyst is DMAP.

When the nucleophilic catalyst is present, compound B and the nucleophilic catalyst can be present in a molar ratio of 1:1 to 1:5, for example at least 1:1, 1:1.5, 1:2, 1:2.5, 1:3, or 1:3.5 and/or up to 1:5, 1:4.5, 1:4, 1:3.5, or 1:3, such as 1:1 to 1:4, 1:2 to 1:5, 1:1.5 to 1:3.5, or 1:1 to 1:3. In some embodiments, the molar ratio of compound B to the nucleophilic catalyst is 1:2.

The protection of the secondary alcohol can occur in an organic solvent. The organic solvent of step (a) can be selected from the group consisting of a nonpolar aromatic solvent, an ether solvent, a chlorinated solvent, acetonitrile, dimethylformamide (DMF), methyl isobutyl ketone (MIBK), 2-butanone, acetone, isopropyl acetate (IPAc), ethyl acetate, and a combination thereof. Nonlimiting examples of nonpolar aromatic solvents include toluene, benzene, xylene, chlorobenzene, fluorobenzene, naphthalene, and benzotrifluoride. Nonlimiting examples of ether solvents include tetrahydrofuran (THF), tetrahydropyran, tetrahydrofurfuryl alcohol, diethyl ether, dibutyl ether, diisopropyl ether, methyl tert-butyl ether (MTBE), 1,2-dimethoxyethane, 1,4-dixoane, 2-methyl-THF, and cyclopentylmethyl ether. Nonlimiting examples of chlorinated solvents include 1,2-dichloroethane, chloroform, carbon tetrachloride, and dichloromethane. Nonlimiting examples of alcohol solvents include methanol, ethanol, propanol, 2-propanol, and tert-butanol.

In some embodiments, the organic solvent is selected from the group consisting of toluene, benzene, xylene, tetrahydrofuran (THF), tetrahydropyran, diethyl ether, dibutyl ether, diisopropyl ether, dimethoxymethane, 1,2-dimethoxyethane, 1,4-dixoane, dichloromethane (DCM), carbon tetrachloride, chloroform, 1,2-dichloroethane, 2-methyltetrahydrofuran (2-MeTHF), methyl tert-butyl ether (MTBE), cyclopentyl methyl ether (CPME), and a combination thereof. In some embodiments, the organic solvent is toluene, THF, DCM, or a combination thereof.

The organic solvent can be included in an amount of 5 L/kg of compound B to 25 L/kg of compound B, for example, at least about 5, 10, 15, or 20 L/kg of compound B and/or up to about 25, 20, 25, or 10 L/kg of compound B, such as, 5 L/kg to 20 L/kg, 5 L/kg to 15 L/kg, or 5 L/kg to 10 L/kg. In some embodiments, the solvent is present in an amount of 10 L/kg of compound B.

Step (a) can occur at a temperature of 20° C. to 100° C., for example, at least 20, 25, 30, 35, 40, 45, 50, or 55° C. and/or up to 100, 95, 90, 85, 80, 75, 70, 65, 60, 55, or 50° C., such as 20° C. to 80° C., 25° C. to 75° C., 30° C. to 70° C., 40° C. to 70° C., 45° C. to 65° C. or 50° C. to 60° C. In some embodiments, step (a) occurs at a temperature of 60° C.

The reaction of compound B with the alcohol protecting group reagent, and optionally the nucleophilic catalyst, forms compound C. As provided herein, compound C has a structure of (C)

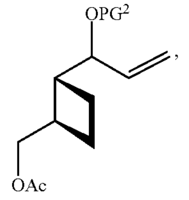

or a salt thereof, wherein $OPG^2$ is a secondary alcohol protecting group. Salts of compound C can be similar to those as described herein for compound B.

As described above, alcohol protecting groups are groups that mask a hydroxyl functional group, and are well known in the art. In some cases, the alcohol protecting group, $OPG^2$, is selected from the group consisting of an ether, an acetal or ketal, an acyl, and a silyl ether.

In some embodiments, $OPG^2$ is an ether. Ether protecting groups comprise an alkyl moiety, either substituted or unsubstituted, attached to the oxygen from the hydroxyl group being protected (e.g., masked as an ether). Examples of suitable ethers include, but are not limited to, methoxy, ethoxy, propoxy, butoxy, tert-butoxy, methoxymethyl acetal (MOM), 2-methyoxyethoxymethyl ester (MEM), ethoxyethyl acetal (EE), and methoxypropyl ether (MOP). Other examples of contemplated ethers include, but are not limited to, benzyloxymethyl acetal (BOM), benzyl ether (Bn), 4-methoxybenzyl ether (PMB), and 2-naphthylmethyl ether (Nap).

In some embodiments, $OPG^2$ is an acetal or ketal. Acetals as a protecting group have a general structure of

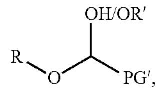

and can be as acetals (as OR' option, where R' is, e.g., an alkyl group) or as hemiacetals (as OH option), where R—O is derived from the hydroxyl group being protected and PG' is the rest of the (hemi)acetal protecting group. Ketals as a protecting group have a general structure of

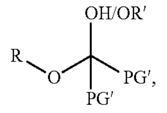

where R—O is derived from the hydroxyl group being protected and can be as ketals (as OR' option, where R' is, e.g., an alkyl group) or as hemiketals (as OH option), and each PG' is derived from the rest of the (hemi)ketal protecting group) mask the hydroxyl group (i.e., R—OH) and can be substituted or unsubstituted. An example of a suitable acetal includes, but is not limited to, tetrahydropyranyl acetal (THP).

In some embodiments, $OPG^2$ is an acyl. As used herein, the term "acyl" refers to an alcohol protecting group in which the oxygen atom of the alcohol is bound to an acyl group —

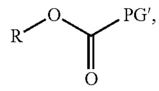

where R—O is derived from the hydroxyl group being protected and PG' is derived from the rest of the acyl protecting group. In some embodiments, the acyl protecting group is selected from the group consisting of acetyl, pivaloyl, benzoyl, 4-bromobenzoyl, 4-fluorobenzoyl, 4-chlorobenzoyl, 4-iodobenzoyl, 4-nitrobenzoyl, 4-phenylbenzoyl, 1-naphthoyl, 2-napthoyl, 4-methoxybenzoyl, and isobutyryl.

In some embodiments, $OPG^2$ is a silyl ether. As used herein, the term "silyl ether" refers to an alcohol protecting group in which the oxygen atom of the alcohol is bound to a silyl ether group

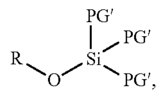

where R—O is derived from the hydroxyl group being protected and each PG' is derived from the rest of the silyl ether protecting group. In some embodiments, the silyl ether protecting group is selected from the group consisting of $OSiEt_3$ (triethylsilyl ether, TES), $OSi(^iPr)_3$ (triisopropylsilyl ether, TIPS), $OSiMe_3$ (trimethylsilyl ether, TMS), $OSiMe_2{}^tBu$ (tert-butyldimethylsilyl ether, TBS), and $OSiPh_2{}^tBu$ (tert-butyldiphenylsilyl ether, TBDPS).

In some embodiments, $OPG^2$ is a sulfonyl protecting group. As used herein, the term "sulfonyl protecting group" refers to an alcohol protecting group in which the oxygen atom of the alcohol is bound to a sulfonyl group —

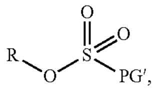

where R—O is derived from the hydroxyl group being protected and PG' is derived from the rest of the sulfonyl protecting group. In some embodiments, the sulfonyl protecting group is selected from the group consisting of mesyl, tosyl, nosyl, and triflyl.

In some embodiments, $OPG^2$ is selected from the group consisting of

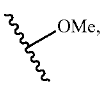

(methoxy)

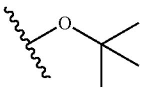

, (tert-butyl ether)

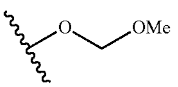

, (methoxymethyl acetal, MOM)

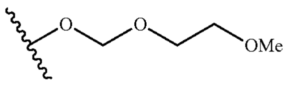

(2-methoxyethoxymethyl ether, MEM),

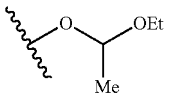

(ethoxyethyl acetal, EE),

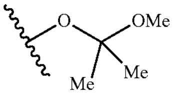

(methoxypropyl acetal, MOP),

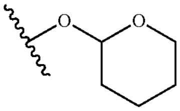

(tetrahydropyranyl acetal, THP),

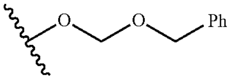

(benzyloxymethyl acetal, BOM),

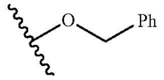

(benzyl ether, Bn),

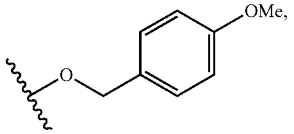

(4-methoxybenzyl ether PMB)

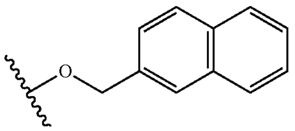

, (2-naphthylmethyl ether, Nap)

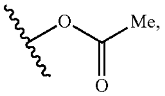

(acetyl, Ac)

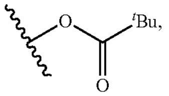

pivaloyl (Piv)

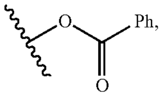

(benzoyl, Bz)

-continued

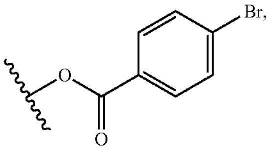

(4-bromobenzoyl, Br-Bz)

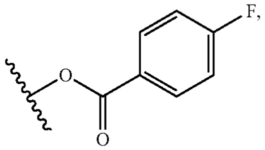

(4-fluorobenzoyl)

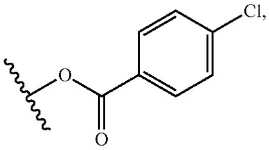

(4-chlorobenzoyl)

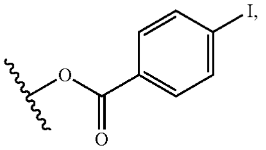

(4-iodobenzoyl)

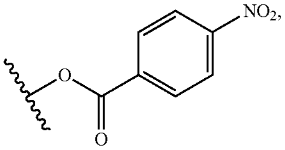

(4-nitrobenzoyl)

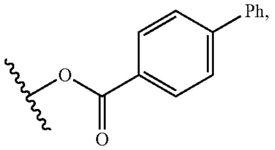

(4-phenylbenzoyl)

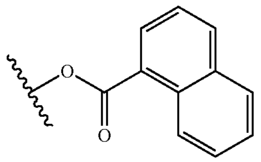

, (1-naphthoyl ester)

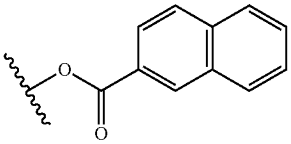

, (2-naphthoyl ester)

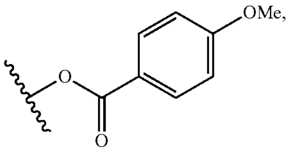

(4-methoxybenzoyl)

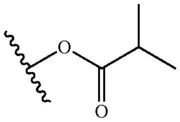

, (isobutyryl)

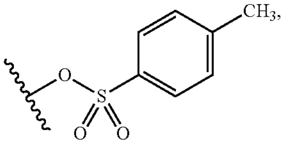

(4-toluenesulfonyl, tosyl)

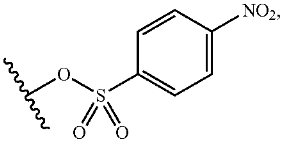

(4-nitrobenzenesulfonyl, nosyl)

and $OSO_2CF_3$ (triflyl). In some embodiments, $OPG^2$ is selected from the group consisting of $OSiEt_3$ (triethylsilyl ether, TES), $OSi({}^iPr)_3$ (triisopropylsilyl ether, TIPS), $OSiMe_3$ (trimethylsilyl ether, TMS), $OSiMe_2{}^tBu$ (tert-butyldimethylsilyl ether, TBS), $OSiPh_2{}^tBu$ (tert-butyldiphenylsilyl ether, TBDPS). In some embodiments, $OPG^2$ is

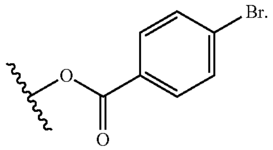 [SMILES: *OC(=O)c1ccc(Br)cc1]

Deprotection of the Primary Alcohol

The processes of the disclosure include removing the acetyl protecting group by admixing compound C, or salt thereof, with a deprotecting agent. The deprotecting agent can be selected to selectively deprotect the primary alcohol while retaining the secondary alcohol protecting group, $OPG^2$. The selection of appropriate protecting groups can be readily determined by one skilled in the art. In some embodiments, the deprotecting agent includes acetyl chloride, an enzyme, an acid, a base, a metal hydride, or a combination thereof.

In some embodiments, the deprotecting agent includes acetyl chloride and an alcohol. As described herein, nonlimiting examples of alcohol solvents include methanol, ethanol, propanol, 2-propanol, and tert-butanol. In some embodiments, the alcohol is selected from the group consisting of methanol, ethanol, propanol, isopropanol, butanol, and a combination thereof. In some embodiments, the alcohol is methanol.

The alcohol can be included in an amount of 3 L/kg of compound C to 15 L/kg of compound C, for example, at least about 3, 5, 7, 10, or 12 L/kg of compound C and/or up to about 15, 12, 10, 7, or 5 L/kg of compound C, such as, 5 L/kg to 15 L/kg, 5 L/kg to 10 L/kg, or 5 L/kg to 7 L/kg. In some embodiments, the solvent is present in an amount of 5.5 L/kg of compound C.

In some embodiments, the deprotecting agent includes a base. Nonlimiting examples of bases include magnesium methoxide, magnesium ethoxide, and aluminum isopropoxide. In some embodiments, the deprotecting agent is magnesium methoxide. In some embodiments, the base is magnesium ethoxide. In some embodiments, the base is aluminum isopropoxide.

In some embodiments, the deprotecting agent includes an enzyme. Nonlimiting examples of suitable enzymes include ester hydrolases (e.g., NOVOZYM® 40086) and lipases (e.g., amino lipase PS). In some embodiments, the enzyme is selected from the group consisting of an ester hydrolase, a lipase, and a combination thereof. In some embodiments, the enzyme is an ester hydrolase. In some embodiments, the enzyme is a lipase.

In some embodiments, the deprotecting agent includes an acid or metal triflate. Nonlimiting examples of suitable acids include hydrochloric acid, sulfuric acid, phosphoric acid, trifluoroacetic acid (TFA), hydrobromic acid, and acetic acid. Nonlimiting examples of suitable metal triflates include ytterbium triflate and dysprosium triflate. In some embodiments, the deprotecting agent is an acid. In some embodiments, the acid is selected from the group consisting of hydrochloric acid, sulfuric acid, phosphoric acid, and a combination thereof. In some embodiments, the acid is hydrochloric acid. In some embodiments, the acid is sulfuric acid. In some embodiments, the acid is phosphoric acid. In some embodiments, the deprotecting agent is a metal triflate. In some embodiments, the metal triflate is ytterbium triflate. In some embodiments, the metal triflate is dysprosium triflate.

In some embodiments, the deprotecting agent includes a metal hydride or a borohydride. A nonlimiting example of a metal hydride is zirconium hydride. A nonlimiting example of a borohydride is lithium triethylborohydride. In some embodiments, the deprotecting agent is zirconium hydride. In some embodiments, the deprotecting agent is lithium triethylborohydride.

Compound C and the deprotecting agent can be present in a molar ratio of 1:0.2 to 1:2, for example, at least about 1:0.2, 1:0.5, 1:0.7, 1:1, or 1:2 and/or up to 1:2, 1:1.7, 1:1.5, 1:1.2, 1:1, or 1:0.7, such as 1:0.2 to 1:1.5, 1:0.1 to 1:1, 1:0.2 to 1:0.7 or 1:0.3 to 1:0.6. In some embodiments, the molar ratio of compound C to the deprotecting agent is 1:0.5.

Step (b) can occur at a temperature of −15° C. to 25° C., for example, at least −15, −10, −5, −2, 0, 2, 5, or 10° C. and/or up to 25, 20, 15, 10, 5, 2, or 0° C., such as −15° C. to 20° C., −10° C. to 15° C., −5° C. to 15° C., or 5° C. to 15° C. In some embodiments, step (b) occurs at a temperature of 10° C.

The removal of the acetyl protecting group of compound C forms compound D:

(D)

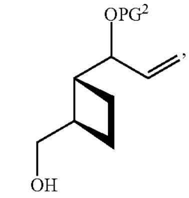

or a salt thereof, wherein $OPG^2$ is as described herein. Salts of compound D can be similar to those as described herein for compound B.

Oxidation of Primary Alcohol

The processes described herein include oxidizing the primary alcohol of compound D, or salt thereof, to form an aldehyde of compound E. The oxidizing includes admixing compound D, or salt thereof, and an oxidizing agent, with an organic solvent, and optionally water.

Suitable oxidizing agents are generally known in the art. Nonlimiting examples of oxidizing agents include peracids such as m-chloroperbenzoic acid (mCPBA), hydrogen peroxide, tert-butyl hydroperoxide and the like; perchlorates such as tetrabutylammonium perchlorate and the like; chlorates such as sodium chlorate and the like; chlorites such as sodium chlorite and the like; hypochlorites such as bleach and the like, periodates such as sodium periodate and the like; a high-valent iodine reagent such as iodosylbenzene, iodobenzenediacetate, and the like; a reagent having manganese, such as manganese dioxide, potassium permanganate and the like; leads such as lead tetraacetate and the like; a reagent having chromium, such as pyridinium chlorochromate (PCC), pyridinium dichromate (PDC), Jones reagents and the like; halogen compounds such as N-bromosuccinimide (NBS) and the like; oxygen; ozone; a sulfur trioxide-pyridine complex; osmium tetroxide; selenium dioxide; 2,3-dichloro-5,6-dicyano-1,4-benzoquinone (DDQ). In some embodiments, the oxidizing agent is selected from the group consisting of oxalyl chloride/DMSO, bleach, $SO_3$/pyridine, iodobenzenediacetate, and any combination thereof. In some embodiments, the oxidizing agent is iodobenzenediacetate.

Compound D and the oxidizing agent can be present in a molar ratio of 1:1.1 to 1:2, for example at least 1:1.1, 1:1.2, 1:1.3, 1:1.4, or 1:1.5 and/or up to 1:2, 1:1.9, 1:1.8, 1:1.7, 1:1.6, or 1:1.5, such as 1:1.1 to 1:1.7, 1:1.1 to 1:1.5, 1:1.1 to 1:1.4, or 1:1.1 to 1:1.3. In some embodiments, the molar ratio of compound D to the oxidizing agent is 1:1.1.

The oxidation of the primary alcohol can further include admixing compound D and the oxidizing reagent with an oxidation catalyst. Nonlimiting examples of oxidation catalysts include 2,2,6,6-tetramethylpiperidin-1-yl)oxidanyl (TEMPO), tetrapropylammonium perruthenate (TPAP), 9-azabicyclo[3.3.1]nonane N-oxyl (ABNO), metal catalysts (e.g., copper, iron, etc.), 2-azaadamantane-N-oxyl, 1-methyl-2-azaadamantane-N-oxyl, 1,3-dimethyl-2-azaadamantane-N-oxyl, and 4-acetamido-2,2,6,6-tetramethylpiperidine-1-oxoammonium tetrafluoroborate. In some embodiments, the oxidation catalyst is selected from the group consisting of 2,2,6,6-tetramethylpiperidin-1-yl)oxidanyl (TEMPO), tetrapropylammonium perruthenate (TPAP)/N-methylmorpholine-N-oxide (NMO), Cu/9-azabicyclo[3.3.1] nonane N-oxyl (ABNO), Fe/ABNO, and a combination thereof. In some embodiments, the oxidation catalyst is TEMPO.

When the oxidation catalyst is present, compound D and the oxidation catalyst can be present in a molar ratio of 1:0.01 to 1:1, for example, at least 1:0.01, 1:0.04, 1:0.05, 1:0.1, 1:0.2, 1:0.3, or 1:0.5 and/or up to 1:1, 1:0.9, 1:0.7, 1:0.5, 1:0.2, or 1:0.1, such as 1:0.01 to 1:0.8, 1:0.01 to 1:0.5, 1:0.01 to 1:0.1, or 1:0.02 to 1:0.05. In some embodiments, the molar ratio of compound D to the oxidation catalyst is 1:0.04.

The oxidation of the primary alcohol can occur in an organic solvent. Suitable organic solvents include those generally described herein. In some embodiments, the organic solvent is selected from the group consisting of a nonpolar aromatic solvent, an ether solvent, a chlorinated solvent, methyl isobutyl ketone (MIBK), 2-butanone, acetone, isopropyl acetate, ethyl acetate, and a combination thereof. In some embodiments, the organic solvent is selected from the group consisting of toluene, benzene, xylene, tetrahydrofuran (THF), tetrahydropyran, diethyl ether, dibutyl ether, diisopropyl ether, dimethoxymethane, 1,2-dimethoxyethane, 1,4-dixoane, dichloromethane (DCM), carbon tetrachloride, chloroform, 1,2-dichloroethane, 2-methyltetrahydrofuran (2-MeTHF), methyl tert-butyl ether (MTBE), cyclopentyl methyl ether (CPME), and a combination thereof. In some embodiments, the organic solvent is toluene.

The organic solvent can be included in an amount of 3 L/kg of compound D to 15 L/kg of compound D, for example, at least about 3, 5, 7, 10, or 12 L/kg of compound D and/or up to about 15, 12, 10, 7, or 5 L/kg of compound D, such as, 5 L/kg to 15 L/kg, 5 L/kg to 10 L/kg, or 5 L/kg to 7 L/kg. In some embodiments, the solvent is present in an amount of 6 L/kg of compound D.

The oxidation of the primary alcohol can occur in the presence of water. When present, compound D and water can be present in a molar ratio of 1:1 to 1:2, for example at least 1:1, 1:1.1, 1:1.2, 1:1.3, 1:1.4, 1:1.5, or 1:1.6 and/or up to 1:2, 1:1.9, 1:1.8, 1:1.7, 1:1.6, or 1:1.5, such as 1:1 to 1:1.7, 1:1 to 1:5, 1:1.1 to 1:1.5, or 1:1 to 1:1.3. In some embodiments, the molar ratio of compound D to water is 1:1.1.

Step (c) can occur at a temperature of 5° C. to 45° C., for example at least 5, 10, 15, 20, 25, or 30° C. and/or up to 45, 40, 35, 30, 25, or 20° C., such as 5° C. to 30° C., 10° C. to 35° C., 15° C. to 30° C., or 15° C. to 25° C. In some embodiments, step (c) occurs at a temperature of 20° C.

The oxidation of compound D, or salt thereof, in step (c) forms compound E:

(E)

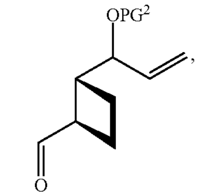

or a salt thereof, wherein $OPG^2$ is as described herein. Salts of compound E can be similar to those as described herein for compound B.

Protection of Aldehyde

The processes of the disclosure include protecting the aldehyde of compound E, or salt thereof, to form a protected aldehyde of compound F, or a salt thereof. The protection of the aldehyde can include admixing compound E, or salt thereof, and an aldehyde protecting group reagent with a solvent.

The term "protected aldehyde" or "aldehyde protecting group" refers to any protecting group used to mask the aldehyde functionality. Aldehyde protecting groups include acetals and hemiacetals. The acetals and hemiacetals can be prepared from $C_{1-8}$ alcohols or $C_{2-8}$ diols. In some cases, the protected aldehyde is a five or six membered cyclic acetal formed from condensation of the aldehyde with ethylene or propylene glycol. In some cases, the protected aldehyde is an imine or hydroxyimine. In some cases, the protected aldehyde comprises a bisulfite or a benzotriazole. In some embodiments, the aldehyde protecting group reagent is selected from the group consisting of benzotriazole, a bisulfite salt (e.g., sodium bisulfite, calcium bisulfite, lithium bisulfite, potassium bisulfite, etc.), a cyanide salt (e.g., sodium cyanide, potassium cyanide, lithium cyanide), hydrogen cyanide, a thiol or dithiol, an alcohol or diol, hydrazine (or alkyl hydrazines), ammonia, and a combination thereof. Other aldehyde protecting group reagents that provide the aldehyde protecting group, $R^1$, described herein are contemplated.

In some embodiments, $R^1$ is selected from the group consisting of

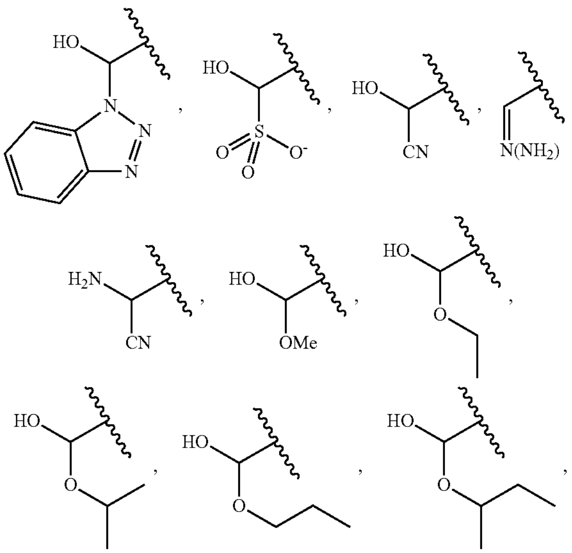

-continued

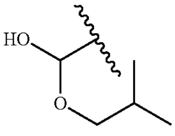, 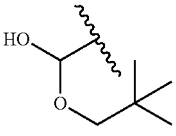, 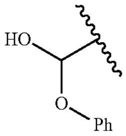,

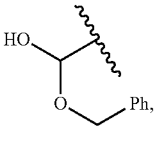 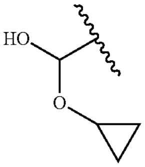, 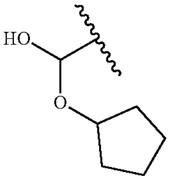,

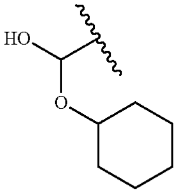, 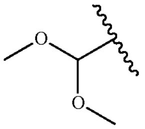, 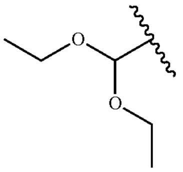,

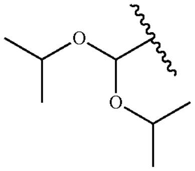, 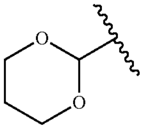, 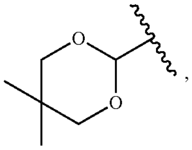,

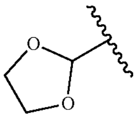, 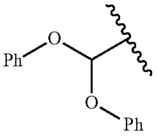, 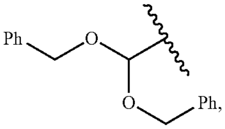

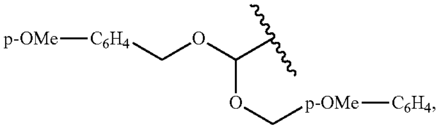

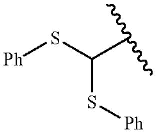, 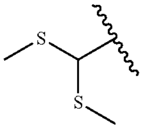, 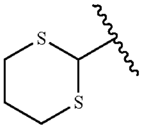,

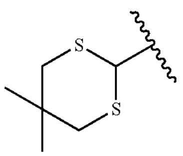, 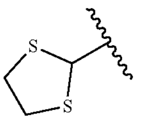, 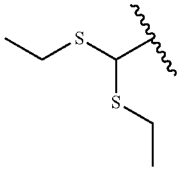,

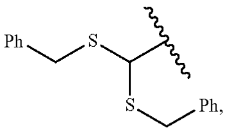

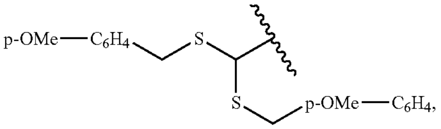

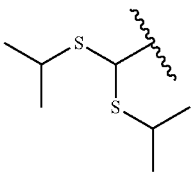, 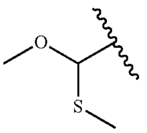, 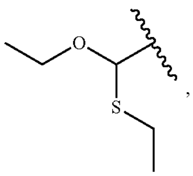,

-continued

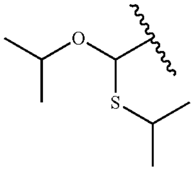, 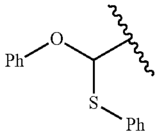,

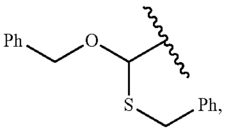

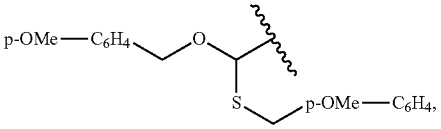

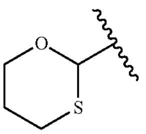, 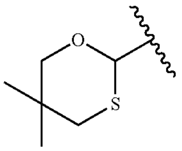, and

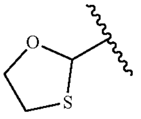.

In some embodiments, $R^1$ is

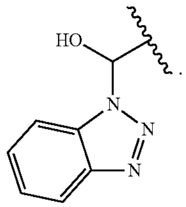 [SMILES: *C(O)n1nnc2ccccc21].

In some embodiments, $R^1$ is

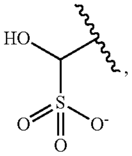 [SMILES: *C(O)S(=O)(=O)[O-]], wherein the counterion is, for example, a sodium ion.

Compound E and the aldehyde protecting group reagent can be present in a molar ratio of 1:1 to 1:1.5, for example at least 1:1, 1:1.1, 1:1.2, or 1:1.3 and/or up to 1:1.5, 1:1.4, 1:1.3, or 1:1.2, such as 1:1 to 1:1.4, 1:1 to 1:1.3, or 1:1.1 to 1:1.3. In some embodiments, the molar ratio of compound E to the aldehyde protecting group reagent is 1:1.

The protection of the aldehyde can include a solvent, which can be selected from the organic solvents generally described herein. In some embodiments, the solvent is selected from the group consisting of toluene, heptane, acetonitrile, water, methyl tert-butyl ether (MTBE), and a combination thereof. In some embodiments, the solvent is selected from the group consisting of toluene/heptane, acetonitrile/water, and methyl tert-butyl ether (MTBE). In some embodiments, the solvent is toluene/heptane. The toluene and heptane can be present in a volume ratio of 1:10 to 10:1, for example 1:8 to 8:1 or 1:2 to 1:2. In some embodiments, the volume ratio of toluene and heptane is 4:7.

Step (d) can occur at a temperature of 20° C. to 50° C., for example at least 20, 25, 30, 35, or 40° C. and/or up to 50, 45, 40, 35, or 30° C., such as 20° C. to 45° C., 25° C. to 45° C., 30° C. to 50° C., 35° C. to 45° C., or 30° C. to 40° C.

The protection of the aldehyde of compound E, or salt thereof, provides compound F:

(F)

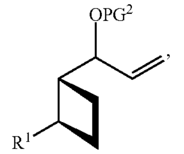

wherein each of $R^1$ and $OPG^2$ are as described herein. Salts of compound F can be similar to those as described herein for compound B.

Crystallization

The processes of the disclosure can further include crystallizing compound F, or a salt thereof. Crystallization can include admixing compound F or salt thereof with a crystallizing solvent to form crystalline compound F or salt thereof. Suitable crystallization solvents are generally known in the art and can include, for example, water, methanol, ethanol, propanol, isopropanol, butanol, diethyl ether, isopropyl ether, methyl tert-butyl ether (MTBE), cyclopentyl methyl ether (CPME), methyl isobutyl ketone (MIBK), pentane, hexane, cyclohexane, heptane, acetone, acetonitrile, tetrahydrofuran, 2-methyl tetrahydrofuran, ethyl acetate, isopropyl acetate, n-butyl acetate, dichloromethane, chloroform, 1,4-dioxane, and mixtures thereof.

In some embodiments, the crystallizing solvent includes heptane, toluene, methyl tert-butyl ether (MTBE), cyclopentyl methyl ether (CPME), methyl isobutyl ketone (MIBK), acetonitrile, isopropyl alcohol, isopropyl acetate, water, or a combination thereof.

The processes for synthesizing compound F or salt thereof, as described herein, can be used to synthesize compounds A1 and A2. As shown in Scheme 4, below, compound F can be used to synthesize compound A1, or salts or solvates thereof. As shown in Scheme 5, below, compound F can be used to synthesize compound A2, or salts or solvates thereof.

Scheme 4-Conversion of Compound F to Compound A1

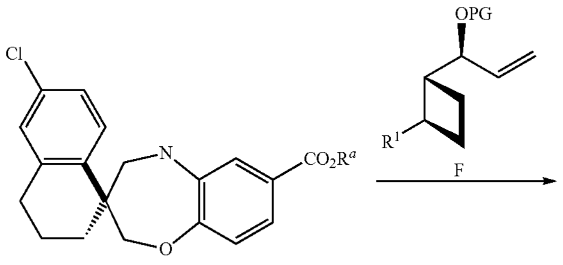

G

-continued

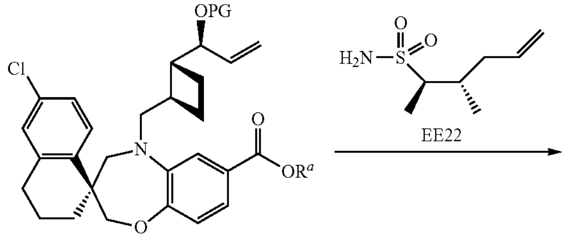

H

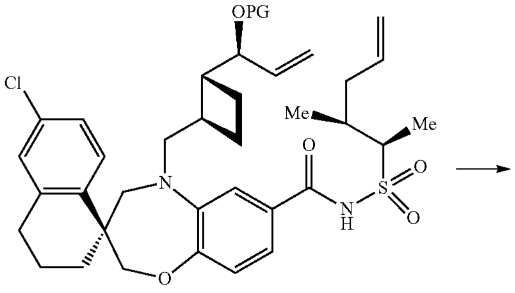

I

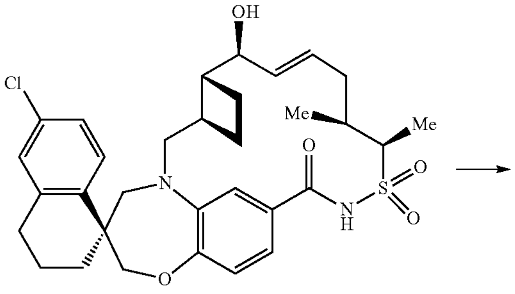

J

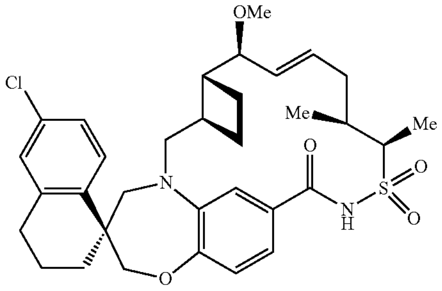

A1

As shown in Scheme 4, compound F can be used to synthesize compound A1 and salts and solvates thereof. The synthesis of compound G and sulfonamide EE22 are disclosed in U.S. Pat. No. 9,562,061. Compounds F and G can be reacted to form the protected vinylic alcohol intermediate, compound H. Compounds EE22 and H can be reacted to form compound I. Cyclization and deprotection of compound I provides compound J which can then be methylated to provide compound A1 as described in U.S. Pat. No. 9,562,061.

Scheme 5-Conversion of Compound F to Compound A2

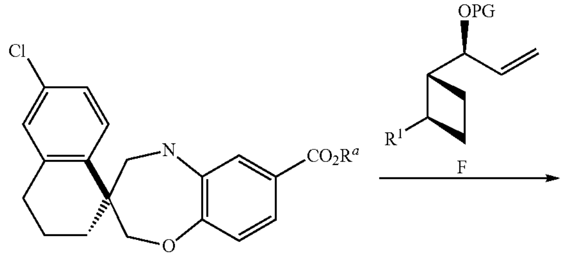

G

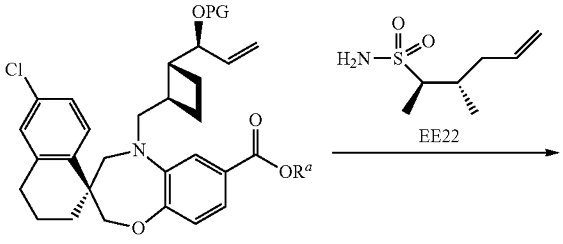

H

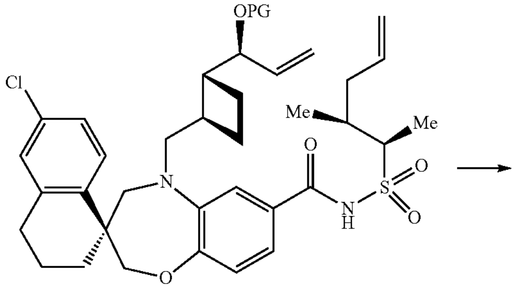

I

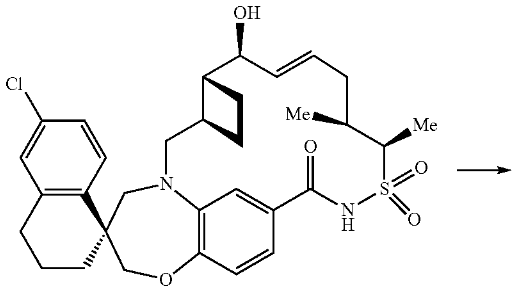

J

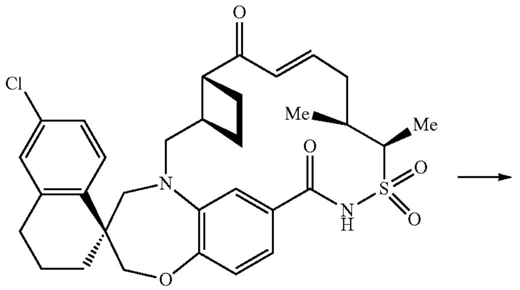

K

-continued

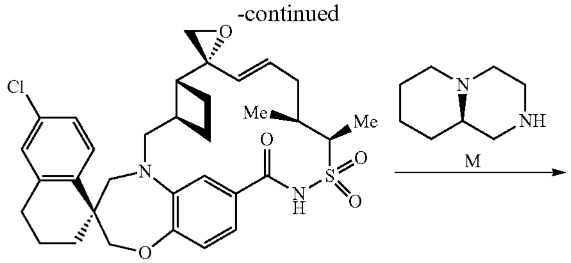

L

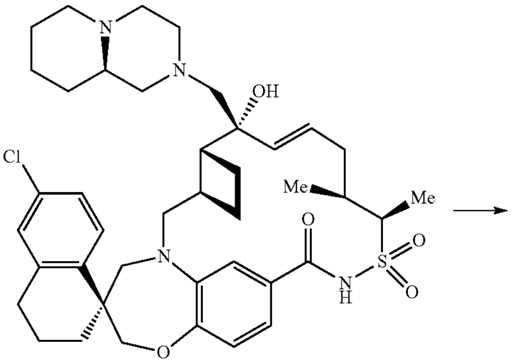

N

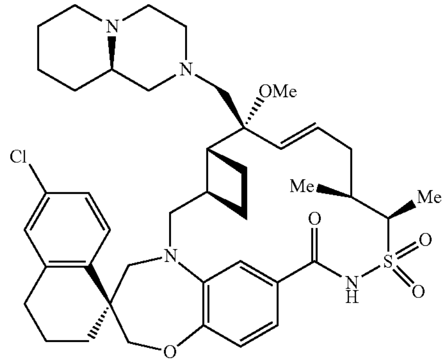

A2

As shown in Scheme 5, compound F can be used to synthesize compound A2 and salts and solvates thereof. As described above with respect to Scheme 4, the synthesis of compound G and sulfonamide EE22 is disclosed in U.S. Pat. No. 9,562,061. Compounds G and F can be reacted to form the protected vinylic alcohol intermediate, compound H. Compounds EE22 and H can be reacted to form compound I which can be cyclized to provide compound J. Compound J can then be oxidized to provide compound K, as disclosed in U.S. Pat. No. 10,300,075. Alternatively, compound I can be oxidized to provide the uncyclized version of compound J, which can then cyclized to provide compound K. Compound K can then be epoxidized to compound L using the procedures disclosed in U.S. Pat. No. 10,300,075. Compound L can then be reacted with bicyclic compound M to provide compound N. Finally, methylation of compound N provides compound A2 as disclosed in U.S. Pat. No. 10,300,075.

In some embodiments, the process further includes synthesizing compound A1 or a salt or solvate thereof using compound F:

(A1)

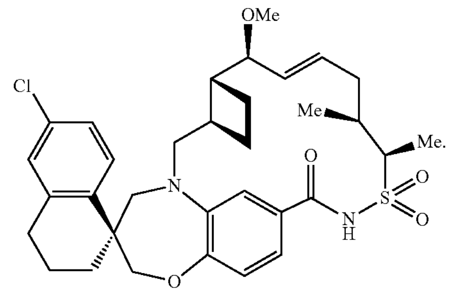

In some embodiments, the process further includes synthesizing compound A2 or a salt or solvate thereof using compound F:

(A2)

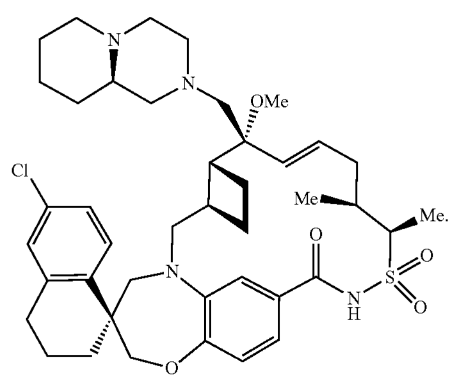

Cyclobutyl Intermediate Compounds

The disclosure also provides compounds having a structure of Formula (I), or a salt thereof:

(I)

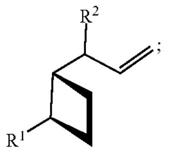

wherein $R^1$ is CHO,

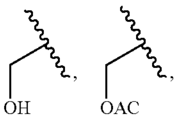

or a protected aldehyde; $R^2$ is OH or $OPG^2$; and $OPG^2$ is a secondary alcohol protecting group, with the proviso that if $R^2$ is OH, then $R^1$ is

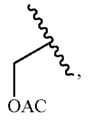

As provided herein, $R^1$ is CHO,

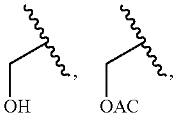

or a protected aldehyde. In some embodiments, $R^1$ is

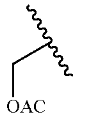

(i.e., an acetyl protected primary alcohol). In some embodiments, $R^1$ is

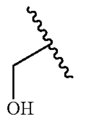

(i.e., a primary alcohol). In some embodiments, $R^1$ is CHO (i.e., an aldehyde).

In some embodiments, $R^1$ is a protected aldehyde. In some embodiments, $R^1$ is selected from the group consisting of

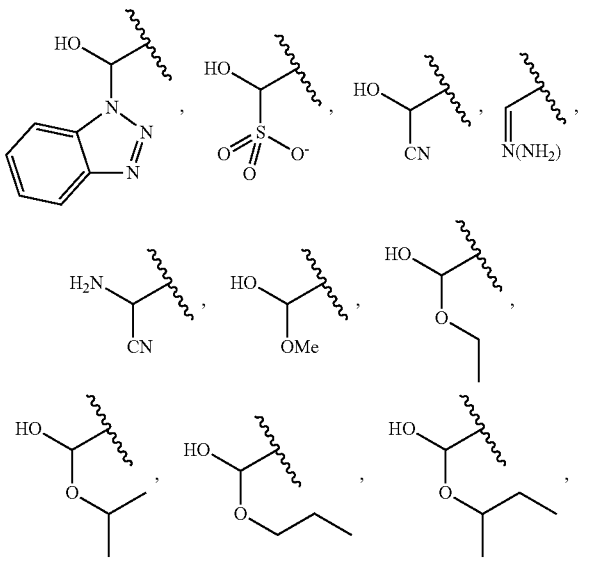

-continued
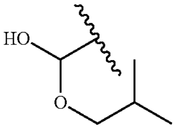, 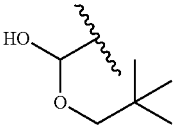, 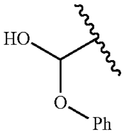,
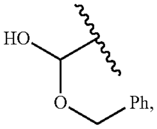 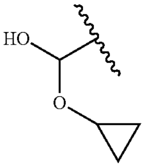, 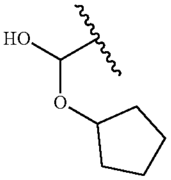,
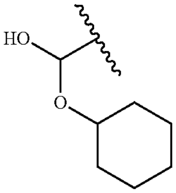, 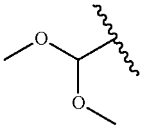, 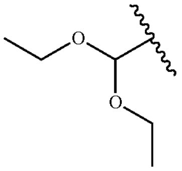,
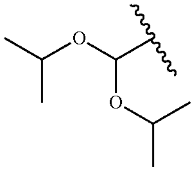, 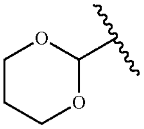, 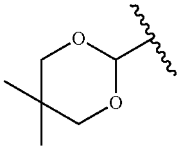,
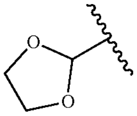, 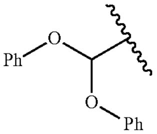, 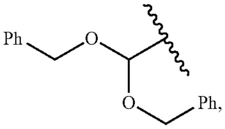
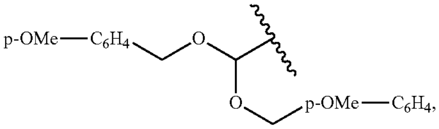
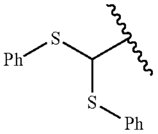, 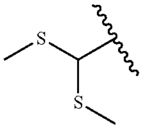, 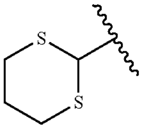,
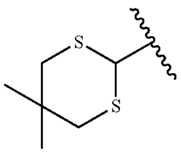, 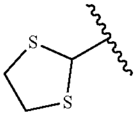, 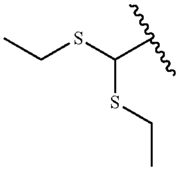,
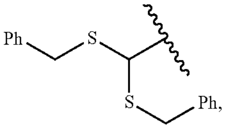
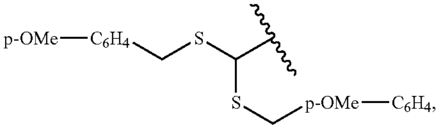
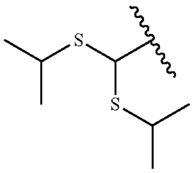, 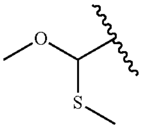, 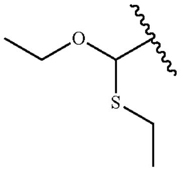,
-continued
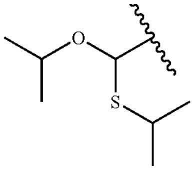, 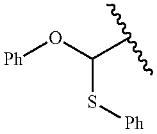,
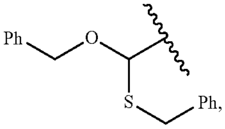
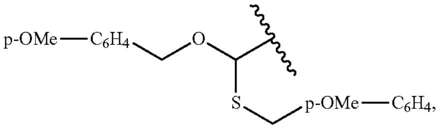
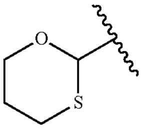, 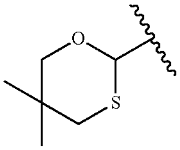, and
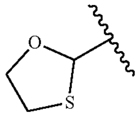.
In some embodiments $R^1$ is
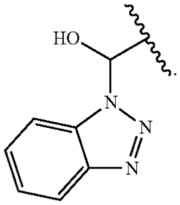 [SMILES: *C(O)n1nnc2ccccc21].
In some embodiments, $R^1$ is
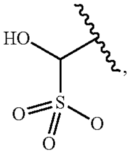,
wherein the counterion is, for example, a sodium ion.
As provided herein, $R^2$ is OH or $OPG^2$. In some embodiments, $R^2$ is OH. When $R^2$ is OH, $R^1$ is
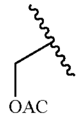

(i.e. the compound has a structure of

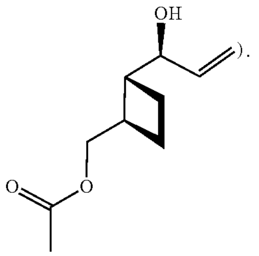

In some embodiments, $R^2$ is $OPG^2$. As described herein, $OPG^2$ is a secondary alcohol protecting group. Suitable secondary alcohol protecting groups include those described herein. For example, in some embodiments, $OPG^2$ is selected from the group consisting of an ether, an acetal or ketal, an acyl, a silyl ether, and a sulfonyl.

In some embodiments, $OPG^2$ is an ether (e.g., methoxy, ethoxy, propoxy, butoxy, tert-butoxy, methoxymethyl acetal (MOM), 2-methyoxyethoxymethyl ester (MEM), ethoxyethyl acetal (EE), and methoxypropyl ether (MOP), benzyloxymethyl acetal (BOM), benzyl ether (Bn), 4-methoxybenzyl ether (PMB), and 2-naphthylmethyl ether (Nap)). In some embodiments, $OPG^2$ is an acetal or ketal (e.g., tetrahydropyranyl acetal (THP)). In some embodiments, $OPG^2$ is an acyl (e.g., acetyl, pivaloyl, benzoyl, 4-bromobenzoyl, 4-nitrobenzoyl, 4-phenylbenzoyl, 1-naphthoyl, 2-napthoyl, 4-methoxybenzoyl, isobutyryl). In some embodiments, $OPG^2$ is a silyl ether (e.g., $OSiEt_3$ (triethylsilyl ether, TES), $OSi(^iPr)_3$ (triisopropylsilyl ether, TIPS), $OSiMe_3$ (trimethylsilyl ether, TMS), $OSiMe_2tBu$ (tert-butyldimethylsilyl ether, TBS), $OSiPh_2{}^tBu$ (tert-butyldiphenylsilyl ether TBDPS)). In some embodiments, $OPG^2$ is a sulfonyl (e.g., mesyl, tosyl, nosyl, triflyl).

In some embodiments, $OPG^2$ is selected from the group consisting of

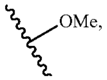
(methoxy)

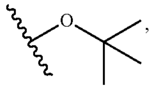
(tert-butyl ether)

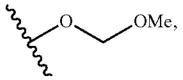
(methoxymethyl acetal, MOM)

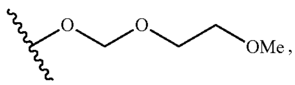
(2-methoxyethoxymethyl ether, MEM)

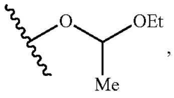
,
(ethoxyethyl acetal, EE)

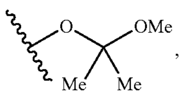
,
(methoxypropyl acetal, MOP)

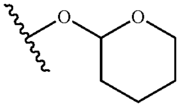
,
(tetrahydropyranyl acetal, THP)

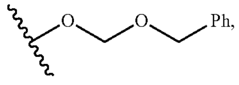
(benzyloxymethyl acetal, BOM)

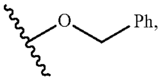
(benzyl ether, Bn)

-continued

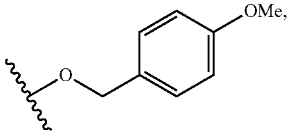
(4-methoxybenzyl ether, PMB)

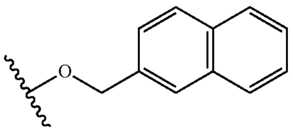
,
(2-naphthylmethyl ether, Nap)

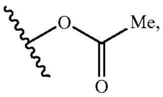
(acetyl, Ac)

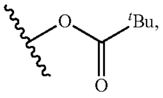
pivaloyl (Piv)

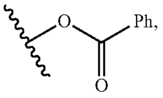
(benzoyl, Bz)

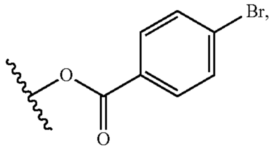
(4-bromobenzoyl, Br-Bz)

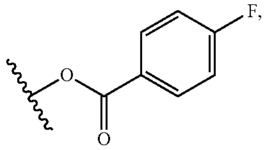
(4-fluorobenzoyl)

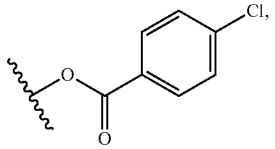
(4-chlorobenzoyl)

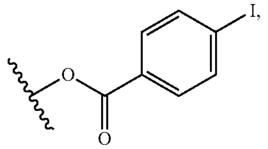
(4-iodobenzoyl)

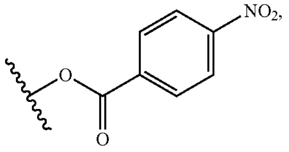
(4-nitrobenzoyl)

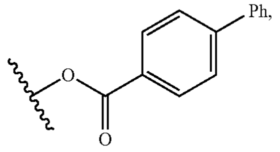
(4-phenylbenzoyl)

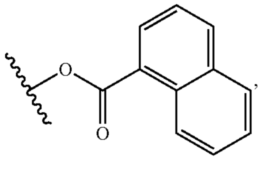
,
(1-naphthoyl ester)

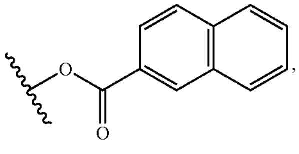
,
(2-naphthoyl ester)

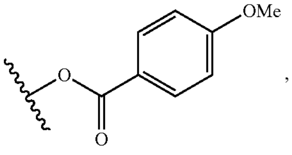
,
(4-methoxybenzoyl)

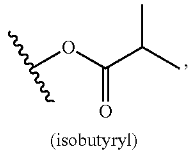
(isobutyryl)

(triethylsilyl ether, TES), $OSi(^iPr)_3$ (triisopropylsilyl ether, TIPS), $OSiMe_3$ (trimethylsilyl ether, TMS), $OSiMe_2tBu$ (tert-butyldimethylsilyl ether, TBS), $OSiPh_2{}^tBu$ (tert-butyldiphenylsilyl ether TBDPS), $OSO_2Me$ (mesyl),

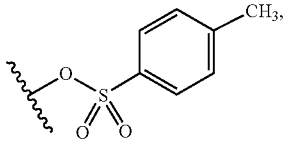

(4-toluenesulfonyl, tosyl),

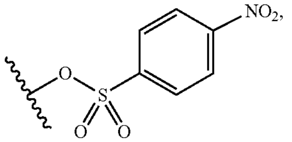

(4-nitrobenzenesulfonyl, nosyl)

and $OSO_2CF_3$ (triflyl). In some embodiments, $OPG^2$ is 4-bromobenzoyl.

In some embodiments, the compound is selected from the group consisting of:

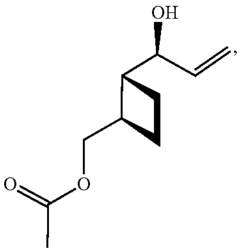

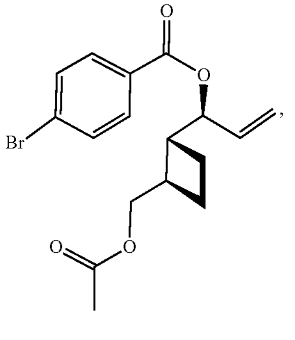

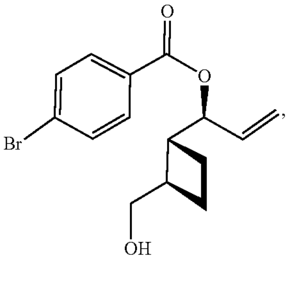

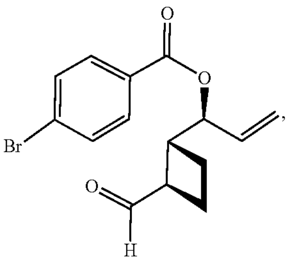

-continued

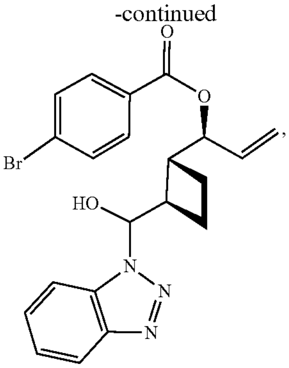

, and

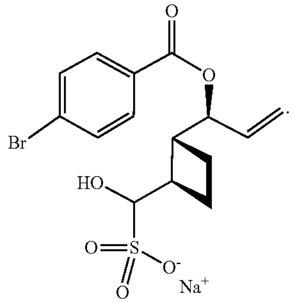

It is to be understood that while the disclosure is read in conjunction with the detailed description thereof, the foregoing description and following example are intended to illustrate and not limit the scope of the disclosure, which is defined by the scope of the appended claims. Other aspects, advantages, and modifications are within the scope of the following claims.

EXAMPLES

The following examples are provided for illustration and are not intended to limit the scope of the invention.

Example 1: Protection of Secondary Alcohol (S)-1-((1R,2R)-2-(acetoxymethyl)cyclobutyl)allyl 4-bromobenzoate was prepared according to the following reaction scheme:

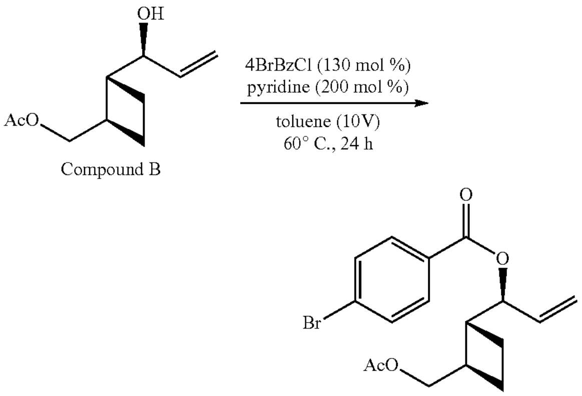

Compound B

Compound C
(wherein $OPG^2$ is 4-bromobenzoyl)

A 3100 L glass-lined reactor was flushed with nitrogen and charged with Compound B (363.5 kg, 25.3 w/w % in toluene, 1.00 equiv.), pyridine (81 L, 2.0 equiv.), and toluene (287 L, 3.1 L/kg). The mixture was stirred at 20° C. until homogenous. A solution of 4-bromobenzoyl chloride (143 kg, 1.30 equiv.) in toluene (380 L, 4.1 L/kg) was then charged to the reaction mixture. The reaction mixture was heated to 60° C. and held 4 hours or until the reaction was adjudged complete by HPLC analysis. The reaction was cooled to 5° C. and quenched with 1 M HCl (367 L, 4 L/kg). The reaction mixture was filtered through a 20 μm filter into a clean 14300 L glass-lined reactor forward rinsing with toluene (184 L, 2 L/kg). The biphasic mixture was warmed to 20° C. and the phases were split. The toluene solution was sequentially washed with sodium bicarbonate solution (5 w/w %, 368 L, 4 L/kg) and water (368 L, 4 L/kg). The toluene solution was then concentrated to a volume of ~184 L, maintaining the internal temperature <40° C. n-Heptane (460 L, 5 L/kg) was charged into the reactor and the resulting solution was cooled to 5° C. After stirring for 1 hour at 5° C., the reaction mixture was filtered through a 0.5 μm sparkler filter into a clean 6700 L glass-lined reactor forward rinsing with n-heptane (110 L, 1.2 L/kg). The mixture was concentrated to a volume of ~262 L, maintaining the internal temperature <40° C. The resulting solution of Compound C was cooled to 20° C. and telescoped directly into the next step.

$^{1}H$ NMR (600 MHz, DMSO) δ 7.92 (d, J=8.5 Hz, 2H), 7.76 (d, J=8.5 Hz, 2H), 5.85 (ddd, J=17.1, 10.6, 6.1 Hz, 1H), 5.42 (ddt, J=8.0, 6.1, 1.4 Hz, 1H), 5.27 (dt, J=17.1, 1.4 Hz, 1H), 5.20 (dt, J=10.6, 1.4 Hz, 1H), 3.97 (dd, J=11.4, 6.0 Hz, 1H), 3.95 (dd, J=11.4, 6.0 Hz, 1H), 2.55-2.49 (m, 1H), 2.47 (qui, J=8.0 Hz, 1H), 1.94-1.87 (m, 2H), 1.87 (s, 3H), 1.72 (dq, J=10.7, 9.1 Hz, 1H), 1.64 (dq, J=11.3, 9.1 Hz, 1H). $^{11}C$ NMR (151 MHz, DMSO) δ 170.3, 164.3, 134.5, 131.9, 131.1, 128.9, 127.5, 117.1, 77.6, 66.6, 40.5, 36.4, 20.5, 20.5, 19.9. LRMS (ESI): Calculated for $C_{17}H_{19}BrO_4$+H: 367, found: 367.

Example 2: Deprotection of Primary Alcohol (S)-1-((1R,2R)-2-(hydroxymethyl)cyclobutyl)allyl 4-bromobenzoate was prepared according to the following reaction scheme:

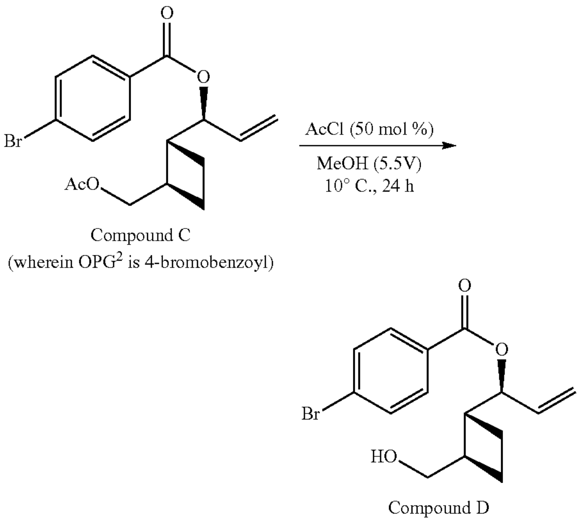

Compound C
(wherein $OPG^2$ is 4-bromobenzoyl)

Compound D
(wherein $OPG^2$ is 4-bromobenzoyl)

A 6700 L glass-lined reactor containing a ~262 L solution of Compound C was charged with methanol (938 L, 5.5 L/kg) and cooled to 1° C. Acetyl chloride (16 L, 0.5 equiv.) was charged at a rate to maintain the internal temperature <5° C. The reaction mixture was stirred at 10° C. for 10 hours or until judged complete by HPLC analysis. The reaction mixture was diluted with toluene (1750 L, 10 L/kg) before being quenched with sodium bicarbonate solution (5 w/w %, 852 L, 5 L/kg) and sodium chloride solution (5 w/w %, 170 L, 1 L/kg). The biphasic mixture was warmed to 20° C. and the phases were separated. The toluene layer was washed with water (852 L, 5 L/kg). The mixture was concentrated to a volume of ~186 L, maintaining the internal temperature <40° C. Compound C (317.5 kg, 48.8 w/w % in toluene) was obtained by HPLC assay and telescoped directly into the next step.

$^{1}H$ NMR (600 MHz, DMSO) δ 7.91 (d, J=8.6 Hz, 2H), 7.76 (d, J=8.6 Hz, 2H), 5.86 (ddd, J=17.2, 10.7, 5.7 Hz, 1H), 5.40 (ddt, J=8.0, 5.7, 1.4 Hz, 1H), 5.26 (dt, J=17.2, 1.4 Hz, 1H), 5.19 (dt, J=10.7, 1.4 Hz, 1H), 4.43 (t, J=5.7 Hz, 1H), 3.36 (dt, J=10.3, 5.7 Hz, 1H), 3.31 (dt, J=10.3, 5.7 Hz, 1H), 2.42 (qui, J=8.0 Hz, 1H), 2.30 (quid, J=8.0, 4.2 Hz, 1H), 1.90-1.77 (m, 2H), 1.73-1.60 (m, 2H). $^{13}C$ NMR (151 MHz, DMSO) δ 164.4, 134.8, 131.9, 131.1, 129.1, 127.4, 116.9, 78.1, 64.0, 40.0, 39.6, 20.4, 19.9. LRMS (ESI): Calculated for $C_{15}H_{17}BrO_3$+H: 325, found: 325.

Example 3: Oxidation of Primary Alcohol (S)-1-((1R,2R)-2-formylcyclobutyl)allyl 4-bromobenzoate was prepared according to the following reaction scheme:

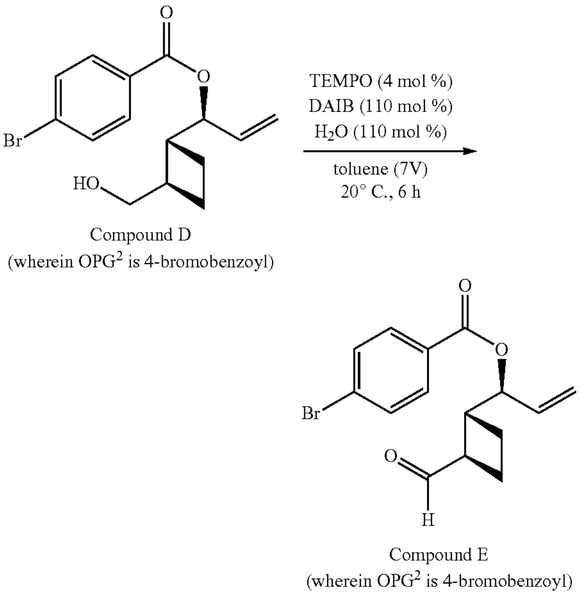

Compound D
(wherein $OPG^2$ is 4-bromobenzoyl)

Compound E
(wherein $OPG^2$ is 4-bromobenzoyl)

A 3600 L stainless steel reactor was flushed with nitrogen and charged with Compound D (317.5 kg, 48.8 w/w % in toluene, 1.00 equiv.) and toluene (930 L, 6 L/kg). The mixture was stirred at 20° C. until homogenous. Water (9.5 L, 1.10 equiv.) and (diacetoxyiodo)benzene (169 kg, 1.10 equiv.) were charged into the reactor. The heterogeneous mixture was cooled to 15° C. A solution of TEMPO (2.9 kg, 0.04 equiv.) in toluene (155 L, 1 L/kg) was charged at a rate to maintain the internal temperature <20° C. The reaction mixture was warmed to 20° C. and held 12 hours or until the reaction was adjudged complete by HPLC analysis. The reaction was quenched with sodium thiosulfate solution (5 w/w %, 775 L, 5.0 L/kg) and the phases were separated. The toluene layer was sequentially washed with sodium carbonate solution (5 w/w %, 775 L, 5.0 L/kg) and twice with water (775 L, 5.0 L/kg). The mixture was concentrated to a volume of ~465 L, maintaining the internal temperature <40° C. The resulting solution of Compound E was cooled to 20° C. and telescoped directly into the next step.

$^1$H NMR (600 MHz, DMSO) δ 9.61 (d, 1.9 Hz, 1H), 7.90 (d, 8.2 Hz, 2H), 7.75 (d, 8.2 Hz, 2H), 5.85 (dddd, 17.3, 10.6, 6.0, 0.6 Hz, 1H), 5.44 (ddt, 7.4, 6.0, 1.4 Hz, 1H), 5.30 (dtd, 17.3, 1.4, 0.6 Hz, 1H), 5.22 (dq, 10.6, 1.4, 0.6 Hz, 1H), 3.23-3.15 (m, 1H), 2.93-2.85 (m, 1H), 2.11-2.02 (m, 1H), 2.00-1.94 (m, 1H), 1.89-1.82 (m, 2H); $^{13}$C NMR (151 MHz, DMSO) δ 202.2, 164.3, 134.1, 131.9, 131.1, 128.8, 127.5, 117.6, 77.2, 47.3, 38.4, 19.9, 18.0. LRMS (ESI): Calculated for $C_{15}H_{15}BrO_3$+H: 323, found: 323.

Example 4: Protection of Aldehyde (1 S)-1-((1R,2R)-2-((1H-Benzo[d][1,2,3]triazol-1-yl)(hydroxy)methyl)cyclobutyl)allyl 4-bromobenzoate was prepared according to the following reaction scheme:

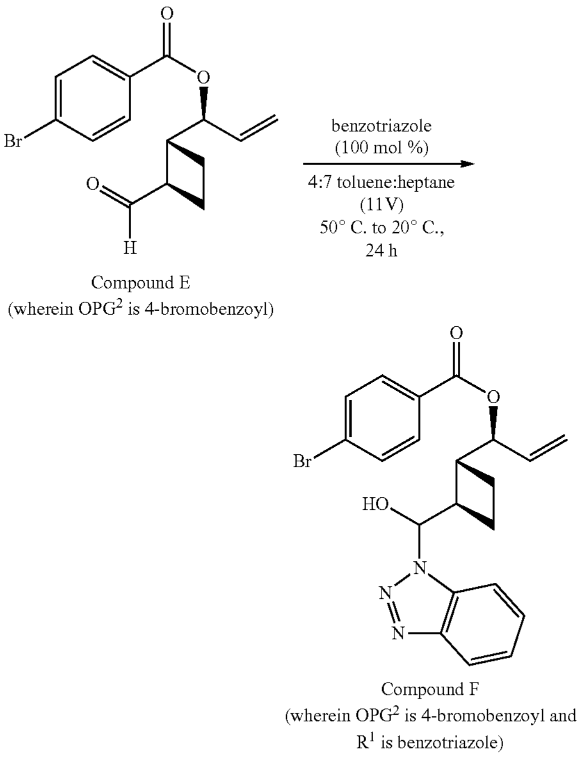

Compound E
(wherein OPG$^2$ is 4-bromobenzoyl)

Compound F
(wherein OPG$^2$ is 4-bromobenzoyl and R$^1$ is benzotriazole)

A 3600 L stainless steel reactor containing a ~465 L solution of Compound E was charged with benzotriazole (56.5 kg, 1.00 equiv.). The mixture was stirred at 20° C. until homogeneous. The resulting solution was filtered through a 0.5 μm polyester filter into a clean 3600 L stainless steel reactor forward rinsing with toluene (155 L, 1 L/kg.). The reaction mixture was heated to 50° C. n-Heptane (310 L, 2 L/kg.) was then charged at a rate to maintain the internal temperature >45° C. Milled Compound F seed (3.2 kg, 2.0 w/w %) was charged into the reactor and the suspension was held at 50° C. for 1 hour. n-Heptane (622.5 L, 4 L/kg) was dosed into the reactor over 10 hours maintaining the internal temperature at 50° C. before starting a cooling ramp to 20° C. over 4 hours. n-Heptane (310 L, 2 L/kg) was dosed into the reactor over 2 hours maintaining the internal temperature at 20° C. before initiating a 4 hours hold. The heterogeneous mixture was transferred into a 1260 L Hastelloy agitated filter dryer and deliquored. The cake was sequentially washed with a 1:1 mixture of toluene:n-heptane (310 L, 2 L/kg) and n-heptane (310 L, 2 L/kg). The cake was dried under vacuum maintaining the internal temperature <50° C. Compound F (170 kg) was isolated by HPLC assay in an 80% molar yield.

$^1$H NMR (600 MHz, DMSO) δ 8.01 (dt, J=8.3, 1.0 Hz, 1H), 7.92 (d, J=8.6 Hz, 2H), 7.88 (dt, J=8.3, 1.0 Hz, 1H), 7.73 (d, J=8.6 Hz, 2H), 7.53 (ddd, J=8.3, 6.9, 1.0 Hz, 1H), 7.39 (ddd, J=8.3, 6.9, 1.0 Hz, 1H), 7.22 (d, J=5.8 Hz, 1H), 6.29 (dd, J=8.7, 5.8 Hz, 1H), 5.96 (ddd, J=17.3, 10.6, 6.4 Hz, 1H), 5.57 (tt, J=6.4, 1.2 Hz, 1H), 5.33 (dt, J=17.3, 1.4 Hz, 1H), 5.25 (dt, J=10.6, 1.4 Hz, 1H), 3.20 (qui, J=8.7 Hz, 1H), 2.78 (qui, J=8.7 Hz, 1H), 1.93 (dtd, J=11.6, 8.7, 3.8 Hz, 1H), 1.75 (dq, J=11.6, 8.7 Hz, 1H), 1.62 (ddd, J=11.9, 8.7, 3.8 Hz, 1H), 1.56 (dt, J=11.9, 8.7 Hz, 1H); $^{13}$C NMR (150 MHz, DMSO) δ 164.6, 145.5, 134.3, 131.7, 131.7, 131.2, 129.4, 127.1, 127.0, 123.9, 119.1, 117.7, 111.6, 85.9, 77.4, 41.7, 40.6, 19.4, 19.0. LRMS (ESI): Calculated for $C_{21}H_{20}BrN_3O_3$+H: 442, found: 442.

What is claimed is:

1. A process for synthesizing compound F or a salt thereof:

(F)

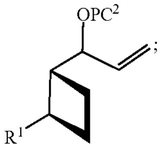

wherein OPG$^2$ is a secondary alcohol protecting group and R$^1$ is a protected aldehyde;

comprising:

(a) protecting a secondary alcohol of compound B, or a salt thereof, by reacting compound B, or salt thereof, with an alcohol protecting group reagent to form compound C, or a salt thereof:

(B)

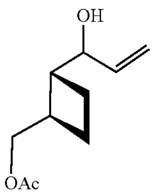

and (C)

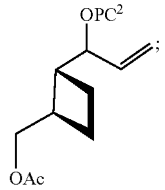

(b) removing compound C's acetyl group to form a primary alcohol of compound D, or a salt thereof:

(D)

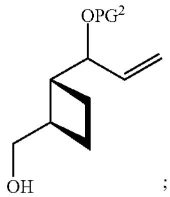

;

(c) oxidizing the primary alcohol of compound D, or salt thereof, to form an aldehyde of compound E, or a salt thereof:

(E)

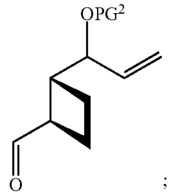

;

and (d) protecting the aldehyde of compound E, or salt thereof, to form a protected aldehyde of compound F, or a salt thereof.

2. The process of claim 1, wherein $OPG^2$ comprises an acyl protecting group, an ether protecting group, acetal or ketal protecting group, a sulfonyl protecting group, or a silyl ether protecting group.

3. The process of claim 2, wherein the acyl protecting group is selected from the group consisting of acetyl, pivaloyl, benzoyl, 4-bromobenzoyl, 4-fluorobenzoyl, 4-chlorobenzoyl, 4-iodobenzoyl, 4-nitrobenzoyl, 4-phenylbenzoyl, 1-naphthoyl, 2-napthoyl, 4-methoxybenzoyl, and isobutyryl.

4. The process of claim 3, wherein the acyl protecting group is 4-bromobenzoyl.

5. The process of claim 2, wherein the alcohol protecting group reagent of step (a) is an acyl chloride or an acyl anhydride.

6. The process of claim 1, wherein compound B and the alcohol protecting group reagent are present in a molar ratio of 1:1 to 1:2.

7. The process of claim 6, wherein the molar ratio of compound B to alcohol protecting group reagent is 1:1.3.

8. The process of claim 2, wherein $OPG^2$ is selected from the group consisting of

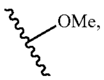

(methoxy)

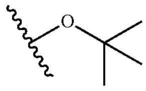

, (tert-butyl ether)

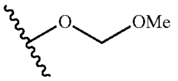

, (methoxymethyl acetal, MOM)

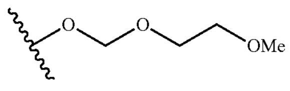

(2-methoxyethoxymethyl ether, MEM),

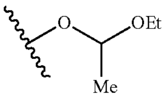

(ethoxyethyl acetal, "EE"),

-continued

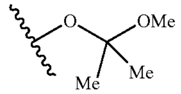

(methoxypropyl acetal, MOP),

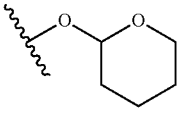

(tetrahydropyranyl acetal, "THP"),

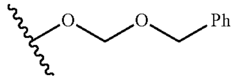

(benzyloxymethyl acetal, BOM),

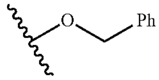

(benzyl ether, Bn),

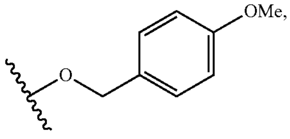

(4-methoxybenzyl ether PMB)

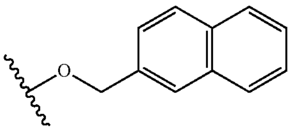

, (2-naphthylmethyl ether, Nap)

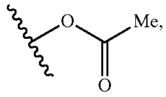

(acetyl, Ac)

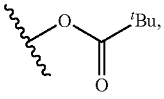

pivaloyl (Piv)

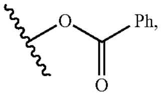

(benzoyl, Bz)

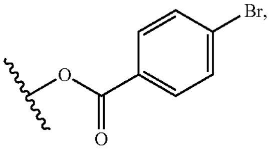

(4-bromobenzoyl, Br-Bz)

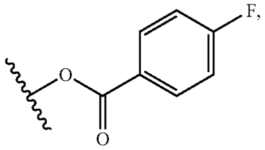

(4-fluorobenzoyl)

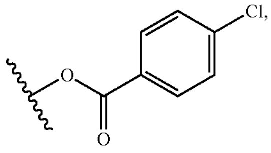

(4-chlorobenzoyl)

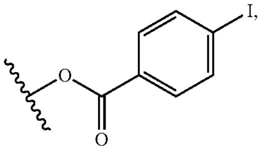

(4-iodobenzoyl)

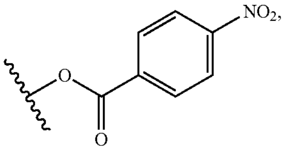

(4-nitrobenzoyl)

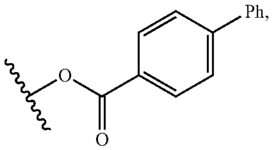

(4-phenylbenzoyl)

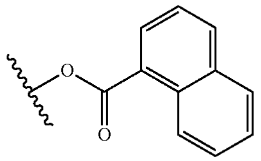

, (1-naphthoyl ester)

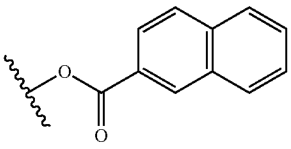

, (2-naphthoyl ester)

-continued

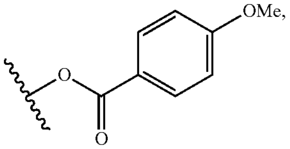

(4-methoxybenzoyl)

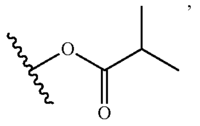

(isobutyryl)

$OSO_2Me$, (mesyl)

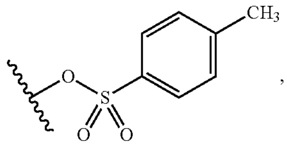

(4-toluenesulfonyl, tosyl)

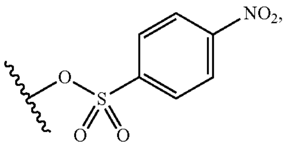

(4-nitrobenzenesulfonyl, nosyl)

and $OSO_2CF_3$ (triflyl).

9. The process of claim 2, wherein the silyl ether protecting group is selected from the group consisting of $OSiEt_3$ (triethylsilyl ether, TES), $OSi(^iPr)_3$ (triisopropylsilyl ether, TIPS), $OSiMe_3$ (trimethylsilyl ether, TMS), OSiMeztBu (tert-butyldimethylsilyl ether, TBS), and $OSiPh_2$ Bu (tert-butyldiphenylsilyl ether TBDPS).

10. The process of claim 2, wherein step (a) comprises admixing compound B, or salt thereof, the alcohol protecting group reagent, and a nucleophilic catalyst.

11. The process of claim 10, wherein the nucleophilic catalyst comprises pyridine, 4-dimethylaminopyridine, or a combination thereof.

12. The process of claim 10, wherein compound B and the nucleophilic catalyst are present in a molar ratio of 1:1 to 1:5.

13. The process of claim 12, wherein the molar ratio of compound B to the nucleophilic catalyst is 1:2.

14. The process of claim 1, wherein step (a) occurs in an organic solvent selected from the group consisting of a nonpolar aromatic solvent, an ether solvent, a chlorinated solvent, acetonitrile, dimethylformamide (DMF), methyl isobutyl ketone (MIBK), 2-butanone, acetone, isopropyl acetate (IPAc), ethyl acetate, and a combination thereof.

15. The process of claim 14, wherein the organic solvent is selected from the group consisting of toluene, benzene, xylene, tetrahydrofuran (THF), tetrahydropyran, diethyl ether, dibutyl ether, diisopropyl ether, dimethoxymethane, 1,2-dimethoxyethane, 1,4-dioxane, dichloromethane (DCM), carbon tetrachloride, chloroform, 1,2-dichloroethane, 2-methyltetrahydrofuran (2-MeTHF), methyl tert-butyl ether (MTBE), cyclopentyl methyl ether (CPME), and a combination thereof.

16. The process of claim 15, wherein the organic solvent is toluene, THF, DCM, or a combination thereof.

17. The process of claim 1, wherein step (a) occurs at a temperature of 20° C. to 100° C.

18. The process of claim 17, wherein step (a) occurs at a temperature of 60° C.

19. The process of claim 1, wherein removing the acetyl protecting group in step (b) comprises admixing compound C, or salt thereof, with a deprotecting agent.

20. The process of claim 19, wherein the deprotecting agent comprises acetyl chloride, an enzyme, an acid, a base, a metal hydride, or a combination thereof.

21. The process of claim 20, wherein the deprotecting agent comprises acetyl chloride and an alcohol.

22. The process of claim 21, wherein the alcohol is selected from the group consisting of methanol, ethanol, propanol, isopropanol, butanol, and a combination thereof.

23. The process of claim 22, wherein the alcohol is methanol.

24. The process of claim 20, wherein the deprotecting agent is magnesium methoxide.

25. The process of claim 20, wherein the deprotecting agent is an enzyme selected from the group consisting of an ester hydrolase, a lipase, and a combination thereof.

26. The process of claim 20, wherein the deprotecting agent is an acid selected from the group consisting of hydrochloric acid, sulfuric acid, phosphoric acid, and a combination thereof.

27. The process of claim 20, wherein the deprotecting agent is zirconium hydride.

28. The process of claim 19, wherein compound C and the deprotecting agent are present in a molar ratio of 1:0.2 to 1:2.

29. The process of claim 28, wherein the molar ratio of compound C to the deprotecting agent is 1:0.5.

30. The process of claim 1, wherein step (b) occurs at a temperature of

−15° C. to 25° C.

31. The process of claim 30, wherein step (b) occurs at a temperature of 10° C.

32. The process of claim 1, wherein oxidizing of step (c) comprises admixing compound D, or salt or solvate thereof, and an oxidizing agent, with an organic solvent, and optionally water.

33. The process of claim 32, wherein the oxidizing agent is selected from the group consisting of oxalyl chloride/DMSO, bleach, $SO_3$/pyridine, iodobenzenediacetate, and any combination thereof.

34. The process of claim 33, wherein the oxidizing agent is iodobenzenediacetate.

35. The process of claim 32, wherein compound D and the oxidizing agent are present in a molar ratio of 1:1.1 to 1:2.

36. The process of claim 35, wherein the molar ratio of compound D to the oxidizing agent is 1:1.1.

37. The process of claim 32, further comprising admixing compound D and the oxidizing reagent with an oxidation catalyst.

38. The process of claim 37, wherein the oxidation catalyst is selected from the group consisting of 2,2,6,6-tetramethylpiperidin-1-yl) oxidanyl (TEMPO), tetrapropylammonium perruthenate (TPAP)/N-methylmorpholine-N-oxide (NMO), Cu/9-azabicyclo[3.3.1]nonane N-oxyl (ABNO), Fe/ABNO, and a combination thereof.

39. The process of claim 38, wherein the oxidation catalyst is TEMPO.

40. The process of claim 37, wherein compound D and the oxidation catalyst are present in a molar ratio of 1:0.01 to 1:1.

41. The process of claim 40, wherein the molar ratio of compound D to the oxidation catalyst is 1:0.04.

42. The process of claim 32, wherein the organic solvent is selected from the group consisting of a nonpolar aromatic solvent, an ether solvent, a chlorinated solvent, methyl isobutyl ketone (MIBK), 2-butanone, acetone, isopropyl acetate, ethyl acetate, and a combination thereof.

43. The process of claim 42, wherein the organic solvent is selected from the group consisting of toluene, benzene, xylene, tetrahydrofuran (THF), tetrahydropyran, diethyl ether, dibutyl ether, diisopropyl ether, dimethoxymethane, 1,2-dimethoxyethane, 1,4-dioxane, dichloromethane (DCM), carbon tetrachloride, chloroform, 1,2-dichloroethane, 2-methyltetrahydrofuran (2-MeTHF), methyl tert-butyl ether (MTBE), cyclopentyl methyl ether (CPME), and a combination thereof.

44. The process of claim 43, wherein the organic solvent is toluene.

45. The process of claim 32, wherein step (c) occurs in the presence of water.

46. The process of claim 45, wherein compound D and water are present in a molar ratio of 1:1 to 1:2.

47. The process of claim 46, wherein the molar ratio of compound D to water is 1:1.1.

48. The process of claim 1, wherein step (c) occurs at a temperature of 5° C. to 45° C.

49. The process of claim 48, wherein step (c) occurs at a temperature of 20° C.

50. The process of claim 1, wherein protecting the aldehyde of compound E, or salt thereof, in step (d) comprises admixing compound E, or salt thereof, and an aldehyde protecting group reagent with a solvent.

51. The process of claim 50, wherein the aldehyde protecting group reagent is selected from the group consisting of benzotriazole, a bisulfite salt, a cyanide salt, hydrogen cyanide, a thiol or dithiol, an alcohol or diol, hydrazine, ammonia, and a combination thereof.

52. The process of claim 50, wherein $R^1$ is selected from the group consisting of

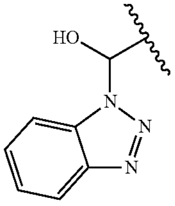 , 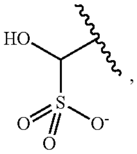 , 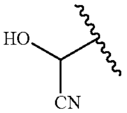 , 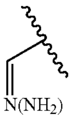 ,

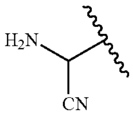 , 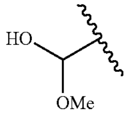 , 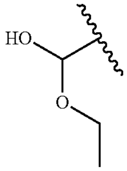 ,

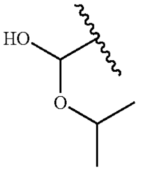 , 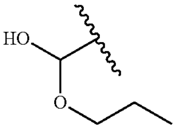 , 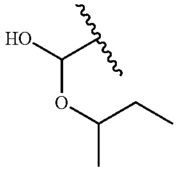 ,

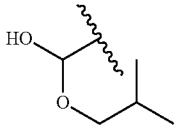 , 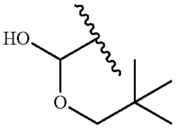 , 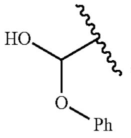 ,

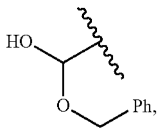 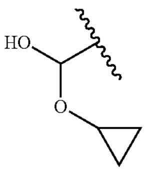 , 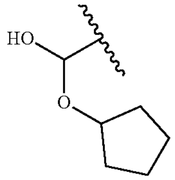 ,

-continued

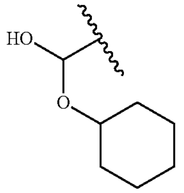 , 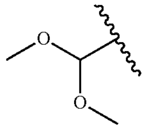 , 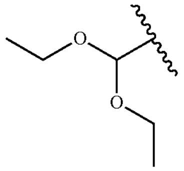 ,

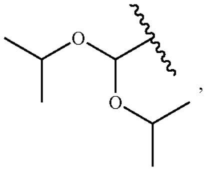 , 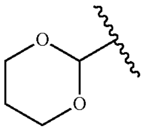 , 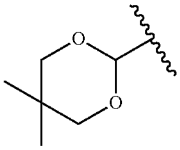 ,

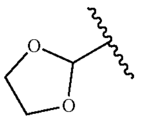 , 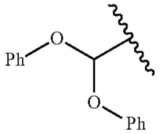 , 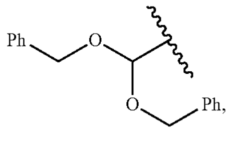

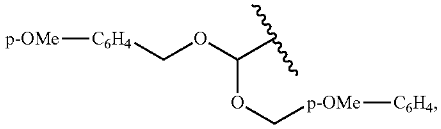

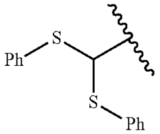 , 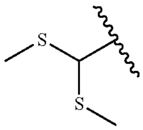 , 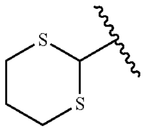 ,

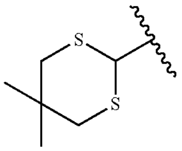 , 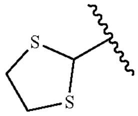 , 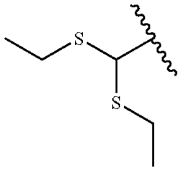 ,

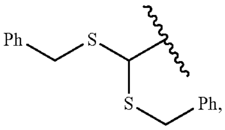

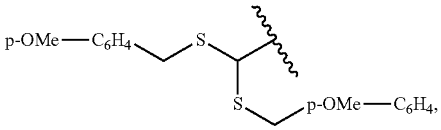

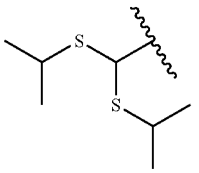 , 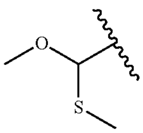 , 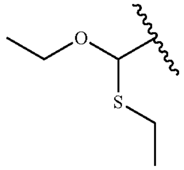 ,

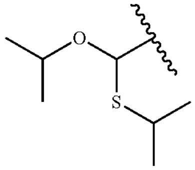 , 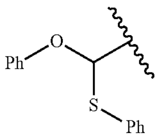 ,

-continued

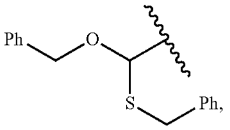

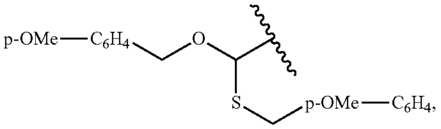

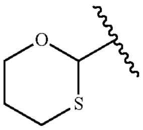

,

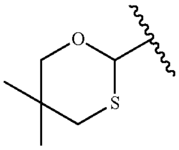

, and

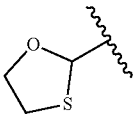

.

53. The process of claim 52, wherein $R^1$ is

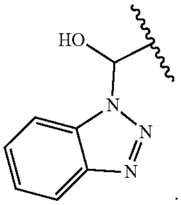 [SMILES: *C(O)n1nnc2ccccc21]

.

54. The process of claim 52, wherein $R^1$ is

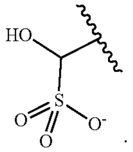

.

55. The process of claim 50, wherein compound E and the aldehyde protecting group reagent are present in a molar ratio of 1:1 to 1:1.5.

56. The process of claim 55, wherein the molar ratio of compound E to the aldehyde protecting group reagent is 1:1.

57. The process of claim 50, wherein the solvent is selected from the group consisting of toluene, heptane, acetonitrile, water, methyl tert-butyl ether (MTBE), and a combination thereof.

58. The process of claim 57, wherein the solvent is selected from the group consisting of toluene/heptane, acetonitrile/water, and methyl tert-butyl ether (MTBE).

59. The process of claim 58, wherein the solvent is toluene/heptane.

60. The process of claim 59, wherein toluene and heptane are present in the solvent as a volume ratio of 4:7.

61. The process of claim 1, wherein step (d) occurs at a temperature of 20° C. to 50° C.

62. The process of claim 1, further comprising:

(e) crystallizing compound F.

63. The process of claim 62, wherein crystallizing comprises admixing compound F with a crystallizing solvent to form crystalline compound F.

64. The process of claim 63, wherein the crystallizing solvent comprises heptane, toluene, methyl tert-butyl ether (MTBE), cyclopentyl methyl ether (CPME), methyl isobutyl ketone (MIBK), acetonitrile, isopropyl alcohol, isopropyl acetate, water, or a combination thereof.

* * * * *